(12) United States Patent
Thompson et al.

(10) Patent No.: US 10,010,307 B2
(45) Date of Patent: *Jul. 3, 2018

(54) SINGLE-INSERTION, MULTIPLE SAMPLING BIOPSY DEVICE WITH LINEAR DRIVE

(71) Applicant: C. R. Bard, Inc., Tempe, AZ (US)

(72) Inventors: Stanley O. Thompson, New Boston, NH (US); Timothy J. Coonahan, Sterling, MA (US); Jon Taylor, Groton, MA (US)

(73) Assignee: C. R. Bard, Inc., Tempe, AZ (US)

( * ) Notice: Subject to any disclaimer, the term of this patent is extended or adjusted under 35 U.S.C. 154(b) by 191 days.

This patent is subject to a terminal disclaimer.

(21) Appl. No.: 14/318,081

(22) Filed: Jun. 27, 2014

(65) Prior Publication Data

US 2014/0371585 A1    Dec. 18, 2014

Related U.S. Application Data

(60) Continuation of application No. 13/592,062, filed on Aug. 22, 2012, now Pat. No. 8,771,200, which is a division of application No. 11/997,403, filed as application No. PCT/US2006/031325 on Aug. 10, 2006, now Pat. No. 8,262,585.

(60) Provisional application No. 60/707,289, filed on Aug. 10, 2005.

(51) Int. Cl.
*A61B 10/02* (2006.01)
*A61B 90/00* (2016.01)

(52) U.S. Cl.
CPC ...... *A61B 10/0275* (2013.01); *A61B 10/0283* (2013.01); *A61B 90/39* (2016.02); *A61B 2010/0208* (2013.01); *A61B 2010/0225* (2013.01); *A61B 2090/3987* (2016.02)

(58) Field of Classification Search
CPC .................................. A61B 2010/0208–10/06
See application file for complete search history.

(56) References Cited

U.S. PATENT DOCUMENTS

| 737,293 | A | 8/1903 | Summerfeldt |
| 1,585,934 | A | 5/1926 | Muir |
| 1,663,761 | A | 3/1928 | Johnson |
| 2,953,934 | A | 9/1960 | Sundt |
| 3,019,733 | A | 2/1962 | Braid |
| 3,224,434 | A | 12/1965 | Molomut et al. |
| 3,289,669 | A | 12/1966 | Dwyer et al. |
| 3,477,423 | A | 11/1969 | Griffith |
| 3,512,519 | A | 5/1970 | Hall |

(Continued)

FOREIGN PATENT DOCUMENTS

| CN | 101011268 A | 8/2007 |
| CN | 101032420 A | 9/2007 |

(Continued)

OTHER PUBLICATIONS

Merriam-Webster.com, Within—Definition and More from the Free Merriam-Webster Dictionary, downloaded Aug. 15, 2014, 3 pages.

(Continued)

*Primary Examiner* — Rene Towa
*Assistant Examiner* — H. Q. Nguyen

(57) ABSTRACT

The present invention provides for exemplary embodiments of a single-insertion, multiple sampling biopsy device. Exemplary embodiments of a single-insertion, multiple sampling device with integrated marker release.

15 Claims, 13 Drawing Sheets

(56) References Cited

U.S. PATENT DOCUMENTS

| | | |
|---|---|---|
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |
| 3,785,380 A | 1/1974 | Brumfield |
| 3,800,783 A | 4/1974 | Jamshidi |
| 3,844,272 A | 10/1974 | Banko |
| 3,882,849 A | 5/1975 | Jamshidi |
| 3,889,682 A | 6/1975 | Denis et al. |
| 3,916,948 A | 11/1975 | Benjamin |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,393,879 A | 7/1983 | Milgrom |
| 4,445,509 A | 5/1984 | Auth |
| 4,490,137 A | 12/1984 | Moukheibir |
| 4,549,554 A | 10/1985 | Markham |
| 4,577,629 A | 3/1986 | Martinez |
| 4,589,414 A | 5/1986 | Yoshida et al. |
| 4,603,694 A | 8/1986 | Wheeler |
| 4,605,011 A | 8/1986 | Naslund |
| 4,616,215 A | 10/1986 | Maddalena |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,678,459 A | 7/1987 | Onik et al. |
| 4,696,298 A | 9/1987 | Higgins et al. |
| 4,702,260 A | 10/1987 | Wang |
| 4,706,687 A | 11/1987 | Rogers |
| 4,776,346 A | 10/1988 | Beraha et al. |
| 4,792,327 A | 12/1988 | Swartz |
| 4,832,044 A | 5/1989 | Garg |
| 4,844,064 A | 7/1989 | Thimsen et al. |
| 4,844,087 A | 7/1989 | Garg |
| 4,850,354 A | 7/1989 | McGurk-Burleson et al. |
| 4,893,635 A | 1/1990 | de Groot et al. |
| 4,907,598 A | 3/1990 | Bauer |
| RE33,258 E | 7/1990 | Onik et al. |
| 4,940,061 A | 7/1990 | Terwilliger et al. |
| 4,952,817 A | 8/1990 | Bolan et al. |
| 4,958,625 A | 9/1990 | Bates et al. |
| 4,967,762 A | 11/1990 | DeVries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,048,538 A | 9/1991 | Terwilliger et al. |
| 5,057,822 A | 10/1991 | Hoffman |
| 5,078,603 A | 1/1992 | Cohen |
| 5,125,413 A | 6/1992 | Baran |
| 5,138,245 A | 8/1992 | Mattinger et al. |
| 5,146,921 A | 9/1992 | Terwilliger et al. |
| 5,156,160 A | 10/1992 | Bennett |
| 5,158,528 A | 10/1992 | Walker et al. |
| 5,172,702 A | 12/1992 | Leigh et al. |
| 5,176,628 A | 1/1993 | Charles et al. |
| 5,183,052 A | 2/1993 | Terwilliger |
| 5,197,484 A | 3/1993 | Kornberg et al. |
| 5,211,627 A | 5/1993 | William |
| 5,223,012 A | 6/1993 | Best et al. |
| 5,225,763 A | 7/1993 | Krohn et al. |
| 5,234,000 A | 8/1993 | Hakky et al. |
| 5,236,334 A | 8/1993 | Bennett |
| 5,242,404 A | 9/1993 | Conley et al. |
| 5,249,583 A | 10/1993 | Mallaby |
| 5,254,117 A | 10/1993 | Rigby et al. |
| 5,282,476 A | 2/1994 | Terwilliger |
| 5,282,477 A | 2/1994 | Bauer |
| 5,290,253 A | 3/1994 | Kira |
| 5,305,762 A | 4/1994 | Acorn et al. |
| 5,324,306 A | 6/1994 | Makower et al. |
| 5,334,183 A | 8/1994 | Wuchinich |
| 5,335,671 A | 8/1994 | Clement |
| 5,368,029 A | 11/1994 | Holcombe et al. |
| 5,368,045 A | 11/1994 | Clement et al. |
| 5,383,874 A | 1/1995 | Jackson et al. |
| 5,397,462 A | 3/1995 | Higashijima et al. |
| 5,400,798 A | 3/1995 | Baran |
| 5,439,474 A | 8/1995 | Li |
| 5,458,112 A | 10/1995 | Weaver |
| 5,469,860 A | 11/1995 | De Santis |
| 5,471,994 A | 12/1995 | Guirguis |
| 5,479,486 A | 12/1995 | Saji |
| 5,485,917 A | 1/1996 | Early |
| 5,492,130 A | 2/1996 | Chiou |
| 5,511,556 A | 4/1996 | DeSantis |
| 5,526,822 A | 6/1996 | Burbank et al. |
| 5,535,755 A | 7/1996 | Heske |
| 5,546,957 A | 8/1996 | Heske |
| 5,554,151 A | 9/1996 | Hinchliffe |
| 5,560,373 A | 10/1996 | De Santis |
| 5,564,436 A | 10/1996 | Hakky et al. |
| 5,569,284 A | 10/1996 | Young et al. |
| 5,575,293 A | 11/1996 | Miller et al. |
| 5,591,170 A | 1/1997 | Spievack et al. |
| 5,601,583 A | 2/1997 | Donahue et al. |
| 5,601,585 A | 2/1997 | Banik et al. |
| 5,602,449 A | 2/1997 | Krause et al. |
| 5,612,738 A | 3/1997 | Kim |
| 5,617,874 A | 4/1997 | Baran |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey et al. |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,779,649 A | 7/1998 | Herbert |
| 5,788,651 A | 8/1998 | Weilandt |
| 5,792,167 A | 8/1998 | Kablik et al. |
| 5,807,282 A | 9/1998 | Fowler |
| 5,817,033 A | 10/1998 | DeSantis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,871,699 A | 2/1999 | Ruggeri |
| 5,879,365 A | 3/1999 | Whitfield et al. |
| 5,908,233 A | 6/1999 | Heskett et al. |
| 5,913,857 A | 6/1999 | Ritchart et al. |
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregoire et al. |
| 5,951,490 A | 9/1999 | Fowler |
| 5,951,575 A | 9/1999 | Bolduc et al. |
| 5,964,716 A | 10/1999 | Gregoire et al. |
| 5,971,939 A | 10/1999 | DeSantis et al. |
| 5,976,164 A | 11/1999 | Bencini et al. |
| 5,980,469 A | 11/1999 | Burbank et al. |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |

(56) References Cited

U.S. PATENT DOCUMENTS

| | | |
|---|---|---|
| 6,027,458 A | 2/2000 | Janssens |
| 6,032,673 A | 3/2000 | Savage et al. |
| 6,036,657 A | 3/2000 | Milliman et al. |
| 6,050,955 A | 4/2000 | Bryan et al. |
| 6,055,870 A | 5/2000 | Jaeger |
| 6,071,247 A | 6/2000 | Kennedy |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,434,507 B1 | 8/2002 | Clayton et al. |
| 6,436,054 B1 | 8/2002 | Viola et al. |
| 6,461,302 B1 | 10/2002 | Thompson |
| 6,471,659 B2 | 10/2002 | Eggers et al. |
| 6,482,158 B2 | 11/2002 | Mault |
| 6,485,436 B1 | 11/2002 | Truckai et al. |
| 6,488,636 B2 | 12/2002 | Bryan et al. |
| 6,488,766 B2 | 12/2002 | Balkum |
| 6,494,844 B1 | 12/2002 | Van Bladel et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,544,194 B1 | 4/2003 | Kortenbach et al. |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1 | 7/2003 | Smith et al. |
| 6,586,585 B1 | 7/2003 | Bastian |
| 6,592,530 B1 | 7/2003 | Farhadi |
| 6,626,849 B2 | 9/2003 | Huitema et al. |
| 6,632,182 B1 | 10/2003 | Treat |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,702,832 B2 | 3/2004 | Ross et al. |
| 6,712,773 B1 | 3/2004 | Viola |
| 6,712,774 B2 | 3/2004 | Voegele et al. |
| 6,752,768 B2 | 6/2004 | Burdorff et al. |
| 6,753,671 B1 | 6/2004 | Harvey |
| 6,755,802 B2 | 6/2004 | Bell |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,850,159 B1 | 2/2005 | Mudge |
| 6,860,860 B2 | 3/2005 | Viola |
| 6,875,183 B2 | 4/2005 | Cervi |
| 6,887,210 B2 | 5/2005 | Quay |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Homer et al. |
| 7,004,174 B2 | 2/2006 | Eggers et al. |
| 7,010,332 B1 | 3/2006 | Irvin et al. |
| 7,025,732 B2 | 4/2006 | Thompson et al. |
| D525,583 S | 7/2006 | Vu |
| 7,108,660 B2 | 9/2006 | Stephens et al. |
| 7,153,274 B2 | 12/2006 | Stephens et al. |
| 7,156,814 B1 | 1/2007 | Williamson, IV et al. |
| 7,182,754 B2 | 2/2007 | Brigham et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,252,641 B2 | 8/2007 | Thompson et al. |
| 7,276,032 B2 | 10/2007 | Hibner |
| 7,328,794 B2 | 2/2008 | Lubs et al. |
| 7,347,828 B2 | 3/2008 | Francese et al. |
| 7,347,829 B2 | 3/2008 | Mark et al. |
| 7,374,544 B2 | 5/2008 | Freeman et al. |
| 7,390,306 B2 | 6/2008 | Mark |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,419,472 B2 | 9/2008 | Hibner et al. |
| 7,432,813 B2 | 10/2008 | Postma |
| 7,452,367 B2 | 11/2008 | Rassman et al. |
| 7,458,940 B2 | 12/2008 | Miller |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,491,177 B2 | 2/2009 | Hibner |
| 7,494,473 B2 | 2/2009 | Eggers et al. |
| 7,497,833 B2 | 3/2009 | Miller |
| 7,510,534 B2 | 3/2009 | Burdorff et al. |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,549,978 B2 | 6/2009 | Carlson et al. |
| 7,575,557 B2 | 8/2009 | Morton et al. |
| 7,648,466 B2 | 1/2010 | Stephens et al. |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,758,515 B2 | 7/2010 | Hibner |
| 7,762,961 B2 | 7/2010 | Heske et al. |
| 7,806,834 B2 | 10/2010 | Beckman et al. |
| 7,828,746 B2 | 11/2010 | Teague |
| 7,828,747 B2 | 11/2010 | Heske et al. |
| 7,841,991 B2 | 11/2010 | Douglas et al. |
| 7,862,517 B2 | 1/2011 | Tsonton et al. |
| 7,871,384 B2 | 1/2011 | Thompson et al. |
| 7,883,476 B2 | 2/2011 | Miller et al. |
| 7,883,494 B2 | 2/2011 | Martin |
| 7,959,580 B2 | 6/2011 | McCullough et al. |
| 7,974,681 B2 | 7/2011 | Wallace et al. |
| 8,002,713 B2 | 8/2011 | Heske et al. |
| 8,012,102 B2 | 9/2011 | McCullough et al. |
| 8,016,772 B2 | 9/2011 | Heske et al. |
| 8,016,844 B2 | 9/2011 | Privitera et al. |
| 8,052,614 B2 | 11/2011 | Heske et al. |
| 8,052,615 B2 | 11/2011 | Reuber et al. |
| 8,073,008 B2 | 12/2011 | Mehta et al. |
| 8,083,671 B2 | 12/2011 | Boulais et al. |
| 8,109,885 B2 | 2/2012 | Heske et al. |
| 8,152,738 B2 | 4/2012 | Li et al. |

(56) References Cited

U.S. PATENT DOCUMENTS

| | | |
|---|---|---|
| 8,157,744 B2 | 4/2012 | Jorgensen et al. |
| 8,162,851 B2 | 4/2012 | Heske et al. |
| 8,172,773 B2 | 5/2012 | Heske et al. |
| 8,190,238 B2 | 5/2012 | Moll et al. |
| 8,206,409 B2 | 6/2012 | Privitera et al. |
| 8,251,917 B2 | 8/2012 | Almazan |
| 8,262,586 B2 | 9/2012 | Anderson et al. |
| 8,267,868 B2 | 9/2012 | Taylor et al. |
| 8,277,393 B2 | 10/2012 | Miller et al. |
| 8,282,574 B2 | 10/2012 | Coonahan et al. |
| 8,283,890 B2 | 10/2012 | Videbaek |
| 8,313,444 B2 | 11/2012 | Thompson et al. |
| 8,343,069 B2 | 1/2013 | Uchiyama et al. |
| 8,366,636 B2 | 2/2013 | Videbaek |
| 8,430,827 B2 | 4/2013 | Nicoson et al. |
| 8,702,621 B2 | 4/2014 | Mccullough et al. |
| 8,702,622 B2 | 4/2014 | McCullough et al. |
| 8,728,004 B2 | 5/2014 | Heske et al. |
| 8,956,306 B2 | 2/2015 | Hibner |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0000403 A1 | 1/2002 | Tanaka et al. |
| 2002/0029007 A1 | 3/2002 | Bryan et al. |
| 2002/0065474 A1 | 5/2002 | Viola |
| 2002/0067151 A1 | 6/2002 | Tanishita |
| 2002/0068878 A1 | 6/2002 | Jasonni et al. |
| 2002/0082518 A1 | 6/2002 | Weiss et al. |
| 2002/0107043 A1 | 8/2002 | Adamson et al. |
| 2002/0115942 A1 | 8/2002 | Stanford et al. |
| 2002/0120212 A1 | 8/2002 | Ritchart et al. |
| 2002/0143269 A1 | 10/2002 | Neuenfeldt |
| 2002/0156395 A1 | 10/2002 | Stephens et al. |
| 2003/0023188 A1 | 1/2003 | Kritzman et al. |
| 2003/0023239 A1 | 1/2003 | Burbank et al. |
| 2003/0073929 A1 | 4/2003 | Baltschun et al. |
| 2003/0093103 A1 | 5/2003 | Malackowski et al. |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0034280 A1 | 2/2004 | Privitera et al. |
| 2004/0049128 A1 | 3/2004 | Miller et al. |
| 2004/0054299 A1 | 3/2004 | Burdorff et al. |
| 2004/0082915 A1 | 4/2004 | Kadan |
| 2004/0092980 A1 | 5/2004 | Cesarini et al. |
| 2004/0092992 A1 | 5/2004 | Adams et al. |
| 2004/0162505 A1 | 8/2004 | Kaplan et al. |
| 2004/0167428 A1 | 8/2004 | Quick et al. |
| 2004/0186393 A1 | 9/2004 | Leigh et al. |
| 2004/0210161 A1 | 10/2004 | Burdorff et al. |
| 2004/0215103 A1 | 10/2004 | Mueller, Jr. et al. |
| 2004/0220495 A1 | 11/2004 | Cahir et al. |
| 2004/0230135 A1 | 11/2004 | Merkle |
| 2004/0230188 A1 | 11/2004 | Cioanta et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0054947 A1 | 3/2005 | Goldenberg |
| 2005/0065453 A1 | 3/2005 | Shabaz et al. |
| 2005/0080355 A1 | 4/2005 | Mark |
| 2005/0085838 A1 | 4/2005 | Thompson et al. |
| 2005/0088120 A1 | 4/2005 | Avis |
| 2005/0101879 A1 | 5/2005 | Shidham et al. |
| 2005/0113715 A1 | 5/2005 | Schwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0275378 A1 | 12/2005 | Canino et al. |
| 2005/0277829 A1 | 12/2005 | Tsonton et al. |
| 2005/0277871 A1 | 12/2005 | Sells |
| 2005/0288605 A1 | 12/2005 | Pellegrino et al. |
| 2006/0030784 A1 | 2/2006 | Miller et al. |
| 2006/0074344 A1 | 4/2006 | Hibner |
| 2006/0074345 A1 | 4/2006 | Hibner |
| 2006/0074350 A1 | 4/2006 | Cash |
| 2006/0113958 A1 | 6/2006 | Lobert et al. |
| 2006/0116603 A1 | 6/2006 | Shibazaki et al. |
| 2006/0122535 A1 | 6/2006 | Daum |
| 2006/0129063 A1 | 6/2006 | Thompson et al. |
| 2006/0149162 A1 | 7/2006 | Daw et al. |
| 2006/0173377 A1 | 8/2006 | McCullough et al. |
| 2006/0178666 A1 | 8/2006 | Cosman et al. |
| 2006/0184063 A1 | 8/2006 | Miller |
| 2006/0200042 A1 | 9/2006 | Weikel, Jr. et al. |
| 2006/0241515 A1 | 10/2006 | Jones et al. |
| 2006/0258956 A1 | 11/2006 | Haberstich et al. |
| 2006/0260994 A1 | 11/2006 | Mark et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0032743 A1 | 2/2007 | Hibner |
| 2007/0055173 A1 | 3/2007 | DeLonzor et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118048 A1 | 5/2007 | Stephens et al. |
| 2007/0118049 A1 | 5/2007 | Viola |
| 2007/0123797 A1 | 5/2007 | Krause |
| 2007/0149893 A1 | 6/2007 | Heske et al. |
| 2007/0149894 A1 | 6/2007 | Heske et al. |
| 2007/0161925 A1 | 7/2007 | Quick et al. |
| 2007/0167736 A1 | 7/2007 | Dietz et al. |
| 2007/0167782 A1 | 7/2007 | Callahan et al. |
| 2007/0167828 A1 | 7/2007 | Saadat |
| 2007/0167943 A1 | 7/2007 | Janssen et al. |
| 2007/0179401 A1 | 8/2007 | Hibner |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0292858 A1 | 12/2007 | Chen et al. |
| 2007/0293788 A1 | 12/2007 | Entrekin et al. |
| 2007/0293830 A1 | 12/2007 | Martin |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0071193 A1 | 3/2008 | Reuber et al. |
| 2008/0079391 A1 | 4/2008 | Schroeck et al. |
| 2008/0103411 A1 | 5/2008 | Van Bladel et al. |
| 2008/0110261 A1 | 5/2008 | Randall et al. |
| 2008/0125634 A1 | 5/2008 | Ryan et al. |
| 2008/0135443 A1 | 6/2008 | Frojd et al. |

(56) References Cited

U.S. PATENT DOCUMENTS

| | | |
|---|---|---|
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0287826 A1 | 11/2008 | Videbaek et al. |
| 2008/0306406 A1 | 12/2008 | Thompson et al. |
| 2008/0319341 A1 | 12/2008 | Taylor et al. |
| 2009/0030405 A1 | 1/2009 | Quick et al. |
| 2009/0048533 A1 | 2/2009 | Miller |
| 2009/0062624 A1 | 3/2009 | Neville |
| 2009/0082695 A1 | 3/2009 | Whitehead |
| 2009/0112118 A1 | 4/2009 | Quick, Jr. et al. |
| 2009/0125062 A1 | 5/2009 | Arnin |
| 2009/0137927 A1 | 5/2009 | Miller |
| 2009/0171242 A1 | 7/2009 | Hibner |
| 2009/0204022 A1 | 8/2009 | Schwindt |
| 2009/0227893 A1 | 9/2009 | Coonahan et al. |
| 2009/0281453 A1 | 11/2009 | Tsonton et al. |
| 2010/0063416 A1 | 3/2010 | Cicenas et al. |
| 2010/0106053 A1 | 4/2010 | Videbaek et al. |
| 2010/0160820 A1 | 6/2010 | Weikel, Jr. et al. |
| 2010/0160823 A1 | 6/2010 | Parihar et al. |
| 2010/0210966 A1 | 8/2010 | Videbaek |
| 2010/0222700 A1 | 9/2010 | Hibner |
| 2011/0021946 A1 | 1/2011 | Heske et al. |
| 2011/0160611 A1 | 6/2011 | Ritchart et al. |
| 2012/0071787 A1 | 3/2012 | Reuber et al. |
| 2012/0095366 A1 | 4/2012 | Heske et al. |
| 2012/0184873 A1 | 7/2012 | Jorgensen et al. |
| 2012/0191009 A1 | 7/2012 | Noon et al. |
| 2012/0238905 A1 | 9/2012 | Heske et al. |
| 2012/0330185 A1 | 12/2012 | Coonahan et al. |
| 2014/0228706 A1 | 8/2014 | Mccullough et al. |
| 2015/0025415 A1 | 1/2015 | Videbaek et al. |
| 2015/0094613 A1 | 4/2015 | Jorgensen et al. |
| 2015/0148702 A1 | 5/2015 | Heske et al. |
| 2015/0190124 A1 | 7/2015 | Mccullough et al. |
| 2015/0238174 A1 | 8/2015 | Reuber et al. |
| 2015/0342579 A1 | 12/2015 | Heske et al. |
| 2016/0256138 A1 | 9/2016 | Videbaek et al. |
| 2016/0367229 A1 | 12/2016 | Jorgensen et al. |
| 2016/0374650 A1 | 12/2016 | Heske et al. |
| 2017/0042517 A1 | 2/2017 | Heske et al. |

FOREIGN PATENT DOCUMENTS

| | | |
|---|---|---|
| DE | 3924291 A1 | 1/1991 |
| DE | 4041614 C1 | 10/1992 |
| DE | 3924291 C2 | 7/2000 |
| DE | 10034297 A1 | 4/2001 |
| DE | 10026303 A1 | 2/2002 |
| DE | 20204363 U1 | 5/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0995400 A1 | 4/2000 |
| EP | 1074271 A2 | 2/2001 |
| EP | 1520518 A2 | 4/2005 |
| EP | 1579809 A1 | 9/2005 |
| EP | 1604615 A1 | 12/2005 |
| EP | 1665989 A2 | 6/2006 |
| EP | 1698282 A1 | 9/2006 |
| EP | 1829487 A1 | 9/2007 |
| EP | 2095772 A1 | 9/2009 |
| EP | 2106750 A2 | 10/2009 |
| EP | 1569561 B1 | 10/2010 |
| FR | 1345429 A | 12/1963 |
| FR | 2739293 A1 | 4/1997 |
| GB | 2018601 A | 10/1979 |
| GB | 2323288 A | 9/1998 |
| JP | 1-126957 A | 9/1987 |
| JP | H10508504 A | 8/1998 |
| JP | 2005530554 A | 10/2005 |
| JP | 2006509545 A | 3/2006 |
| JP | 2006528907 A | 12/2006 |
| JP | 2007502159 A | 2/2007 |
| WO | 9508945 A2 | 4/1995 |
| WO | 9628097 A1 | 9/1996 |
| WO | 9734531 A1 | 9/1997 |
| WO | 9825522 A1 | 6/1998 |
| WO | 9831285 A1 | 7/1998 |
| WO | 9835615 A1 | 8/1998 |
| WO | 9846290 A1 | 10/1998 |
| WO | 9933501 A1 | 7/1999 |
| WO | 0004832 A1 | 2/2000 |
| WO | 0030546 A1 | 6/2000 |
| WO | 0059378 A2 | 10/2000 |
| WO | 0172230 A1 | 10/2001 |
| WO | 0222023 A1 | 3/2002 |
| WO | 0232318 A1 | 4/2002 |
| WO | 02069808 A2 | 9/2002 |
| WO | 2005013830 A1 | 2/2005 |
| WO | 2006015302 A1 | 2/2006 |
| WO | 2007047128 A1 | 4/2007 |
| WO | 2007095330 A2 | 8/2007 |
| WO | 2007112751 A2 | 10/2007 |
| WO | 2008021687 A1 | 2/2008 |
| WO | 2008024684 A2 | 2/2008 |
| WO | 2008040812 A1 | 4/2008 |
| WO | 2008131362 A2 | 10/2008 |
| WO | 2013158072 A1 | 10/2013 |

OTHER PUBLICATIONS

Merriam-Webster.com, Series—Definition and More from the Free Merriam-Webster Dictionary, downloaded Aug. 15, 2014, 3 pages.
Merriam-Webster.com, Restrain—Definition and More from the Free Merriam-Webster Dictionary, downloaded Aug. 17, 2014, 3 pages.
Merriam-Webster.com, While—Definition and More from the Free Merriam-Webster Dictionary, downloaded Aug. 17, 2014, 4 pages.

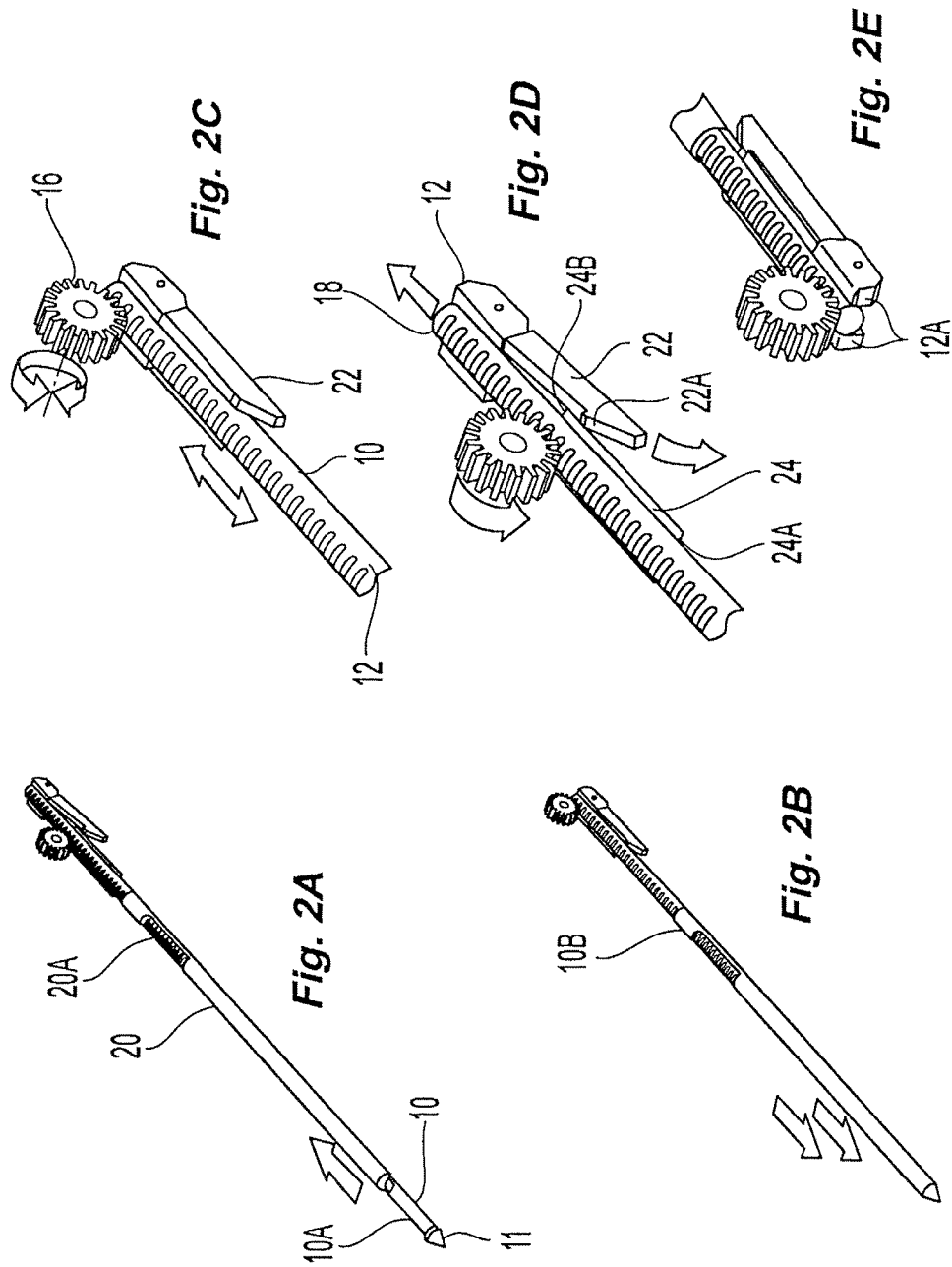

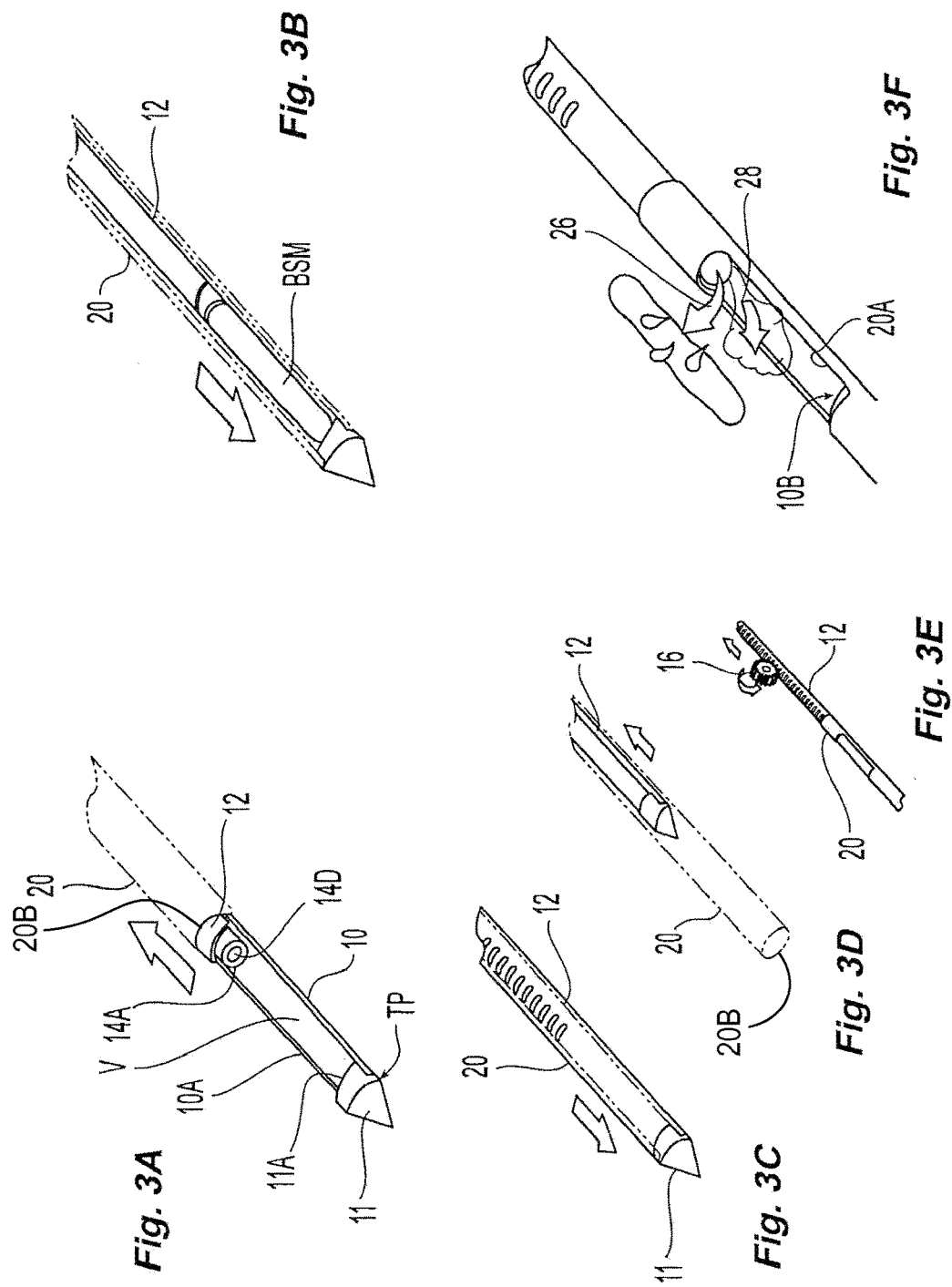

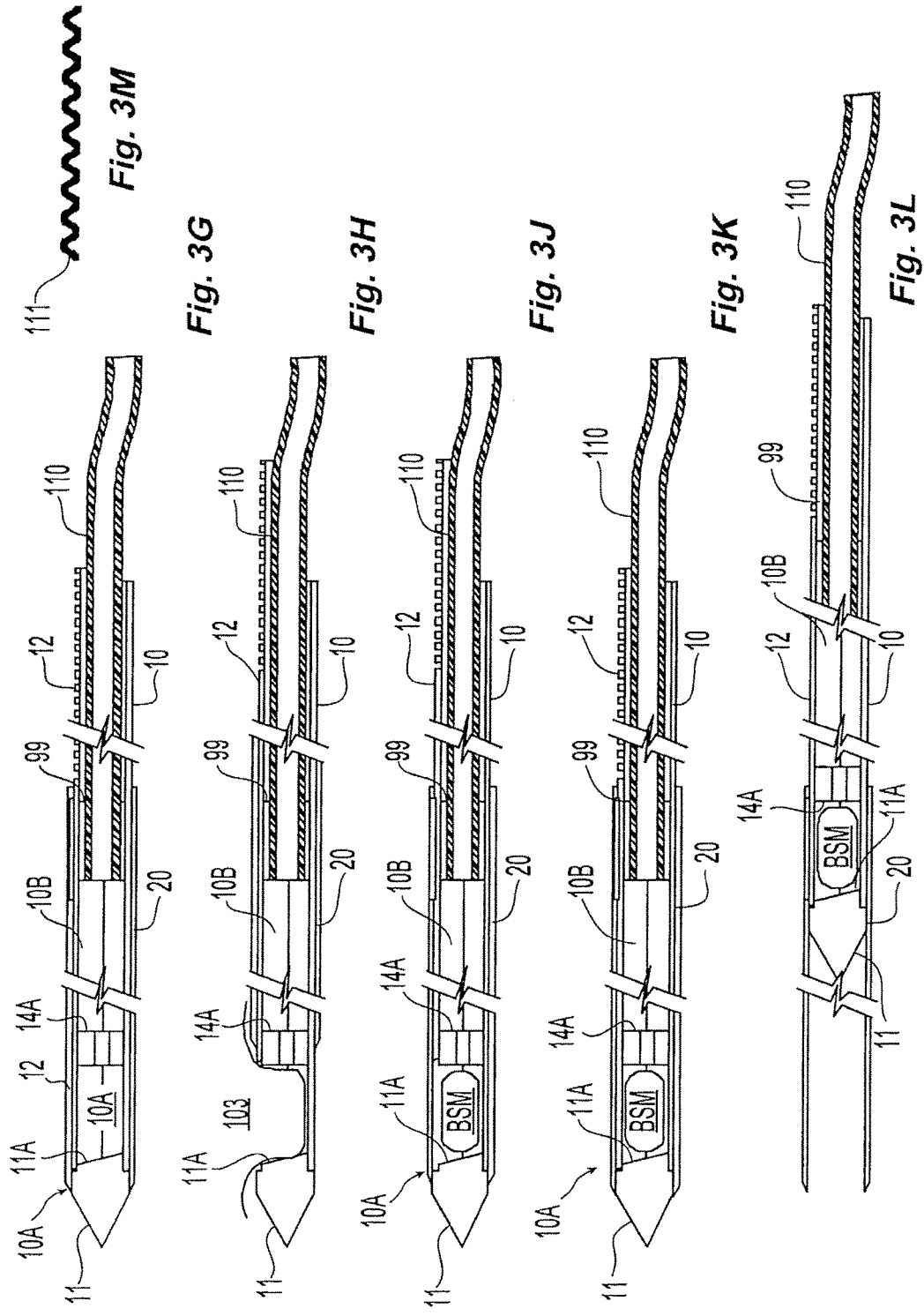

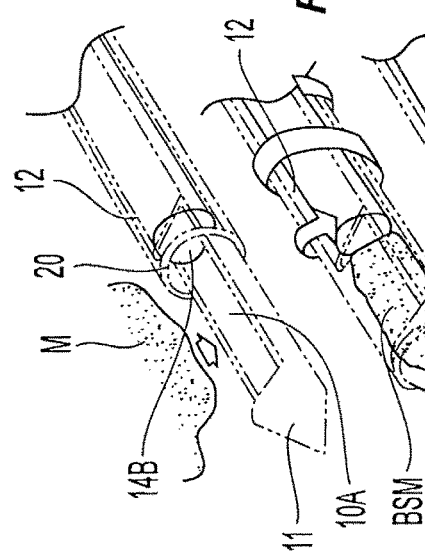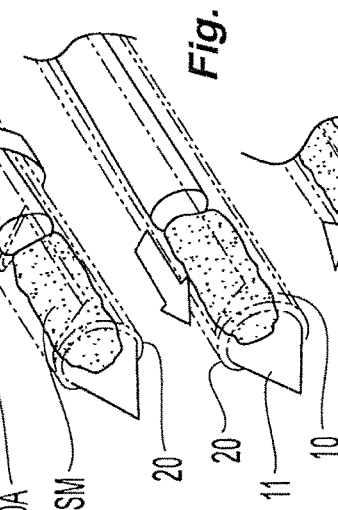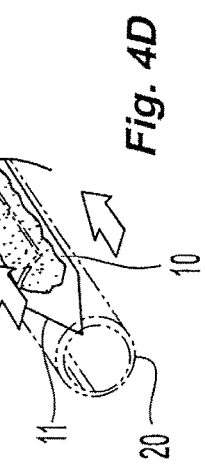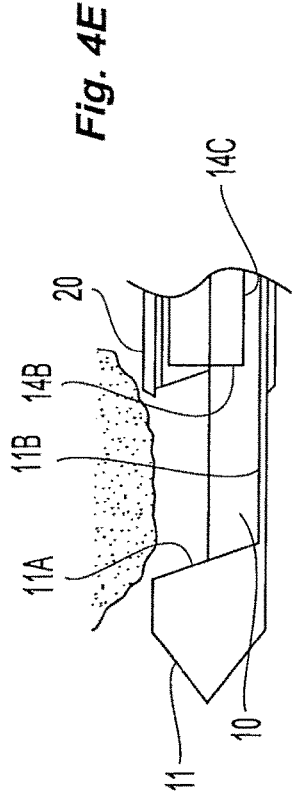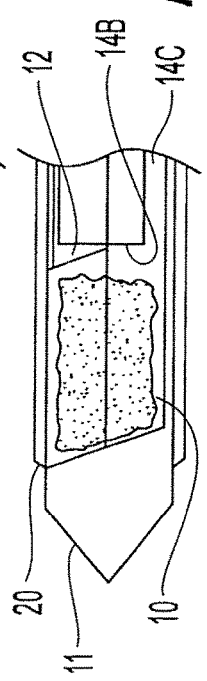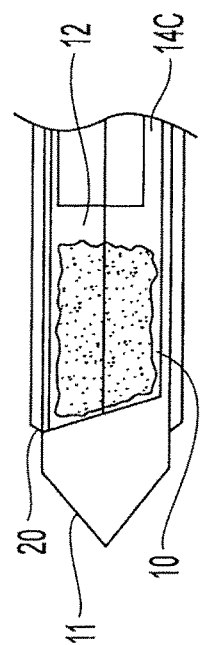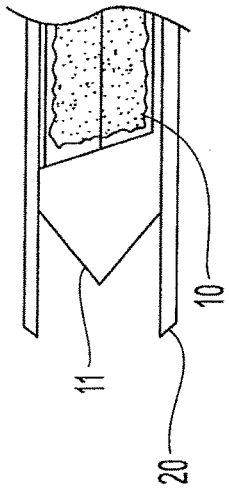

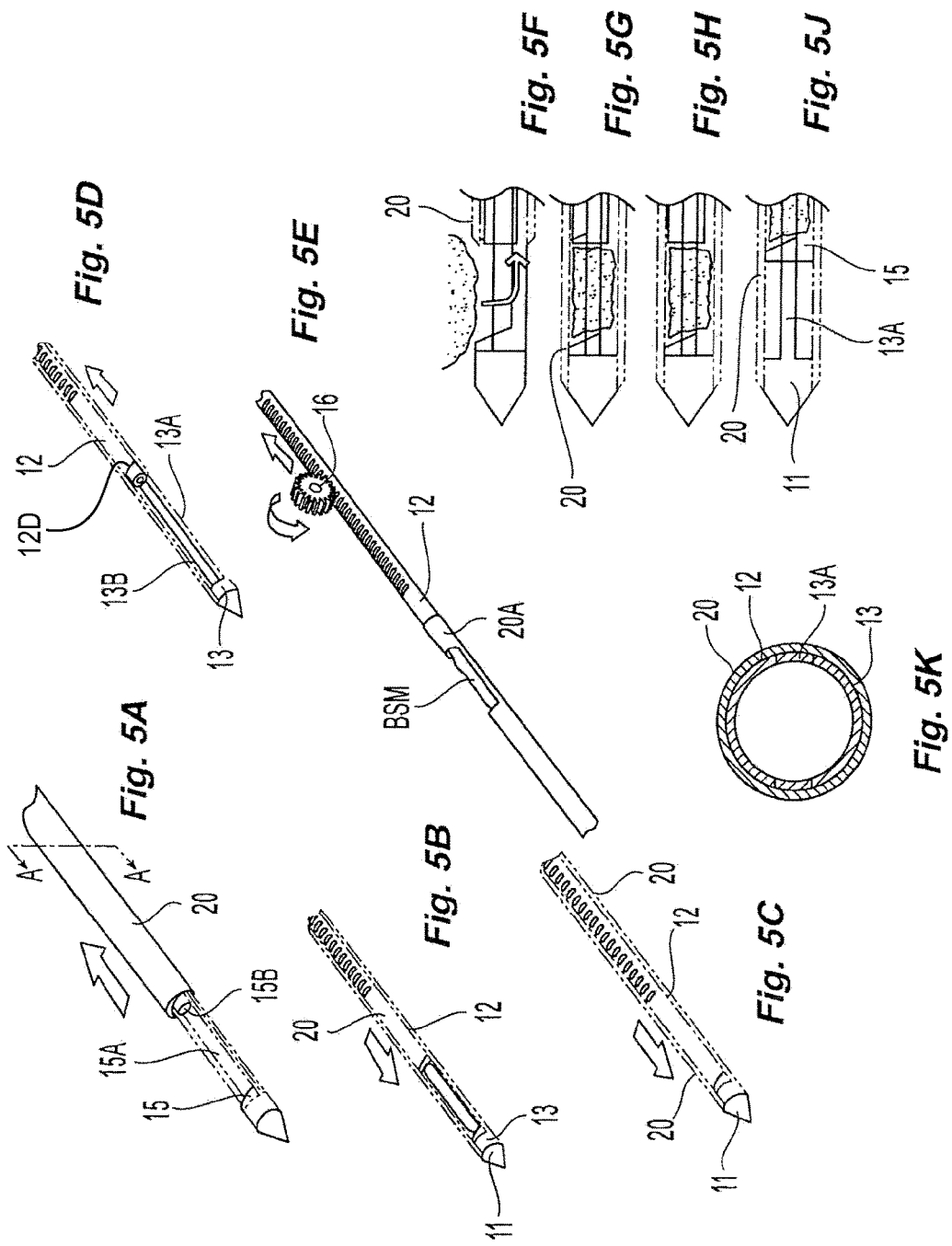

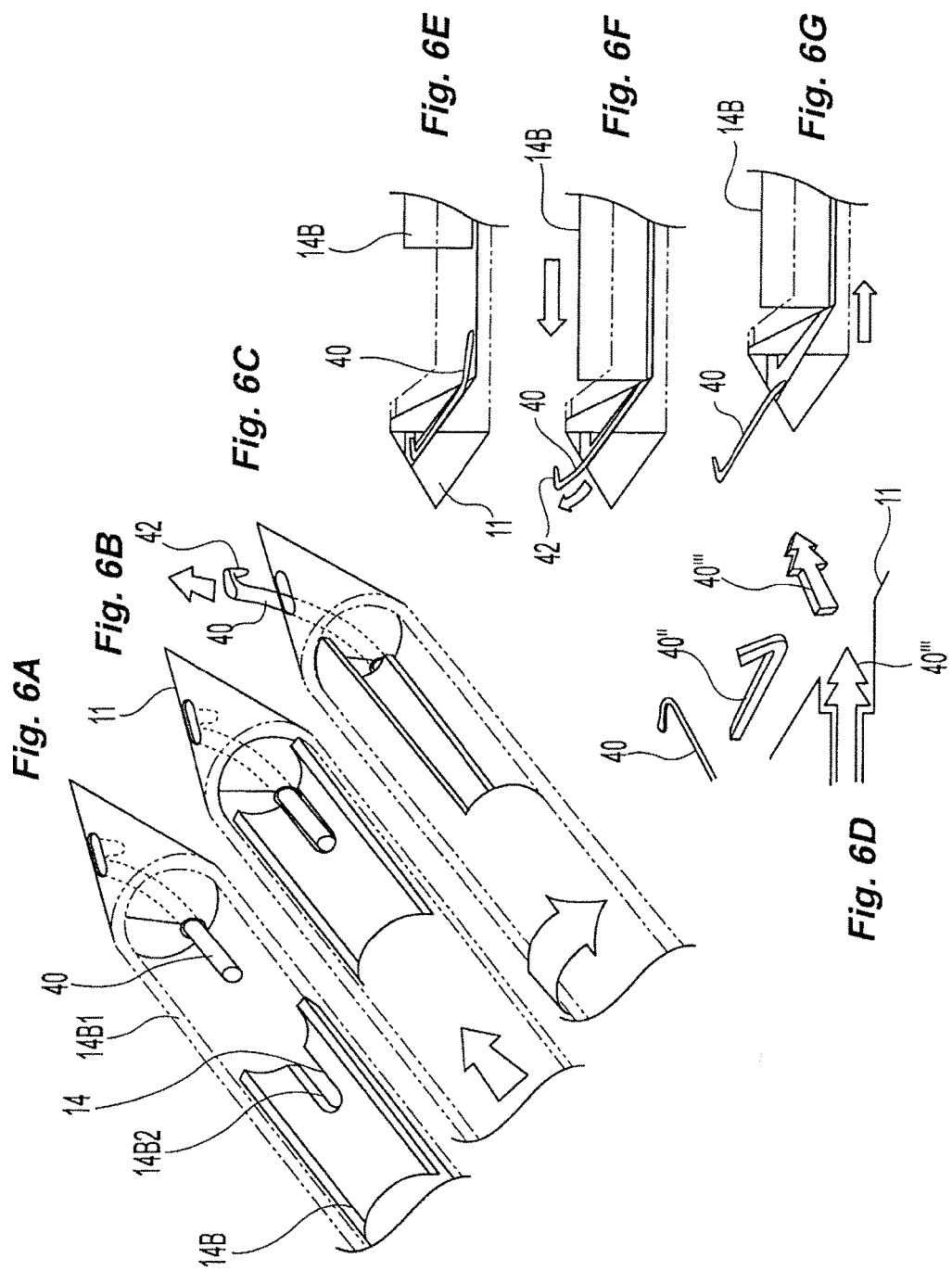

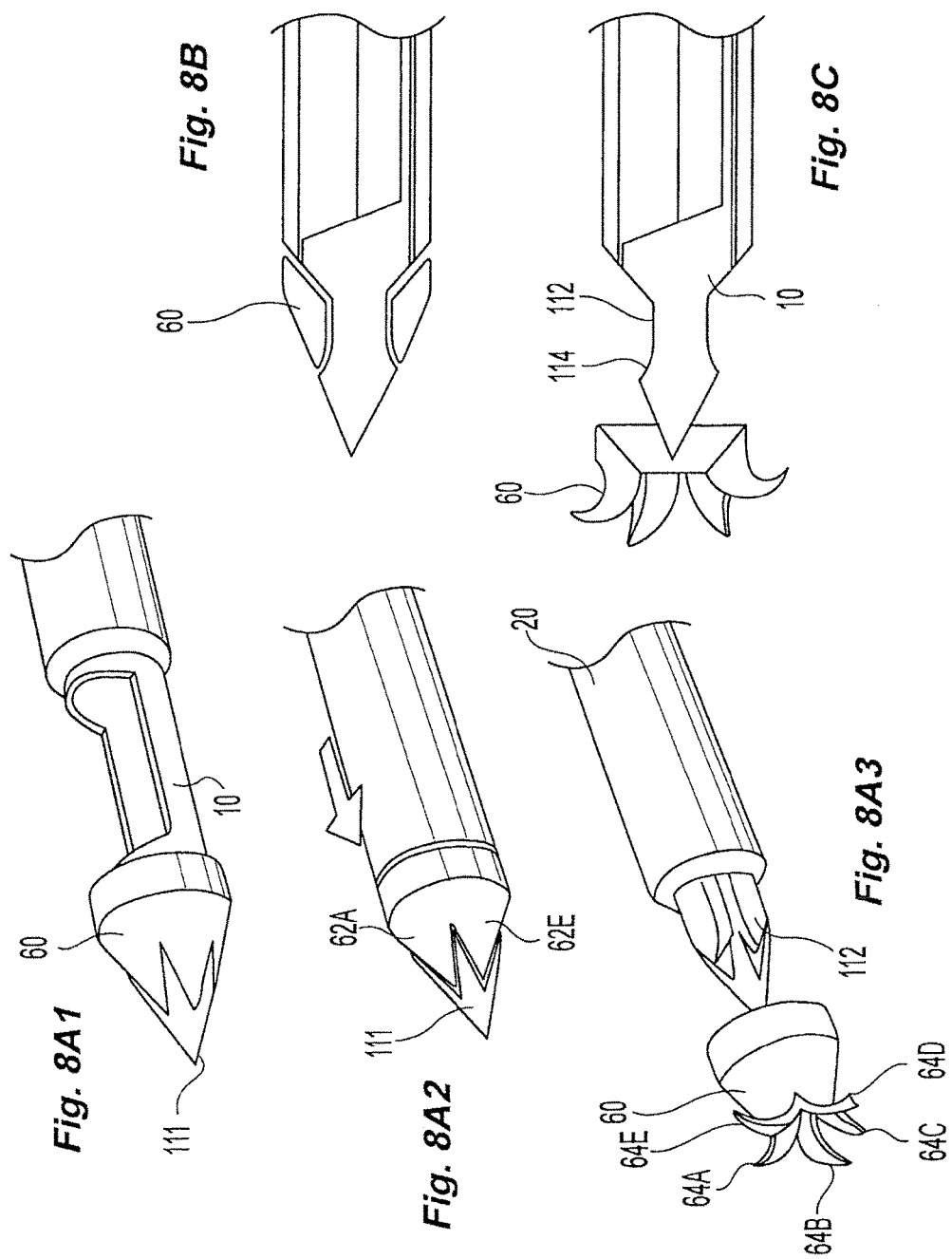

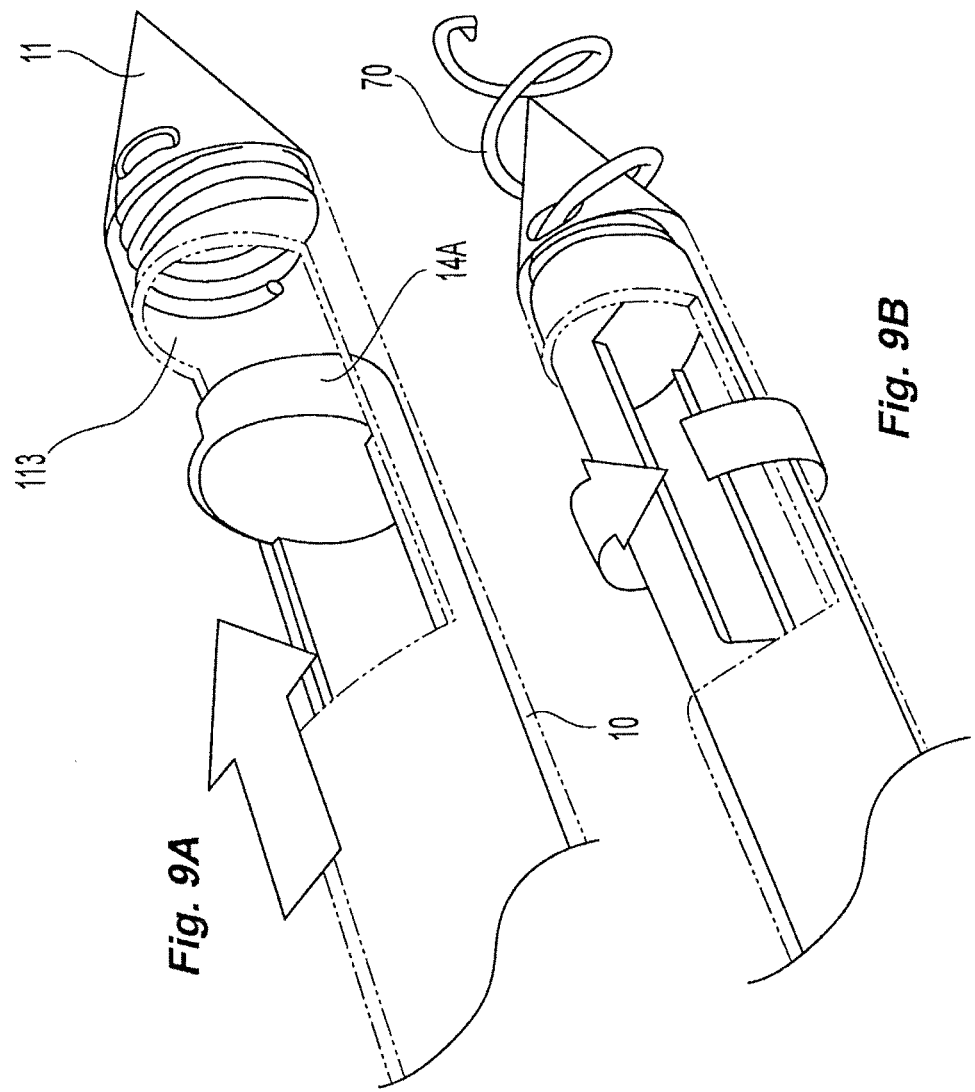

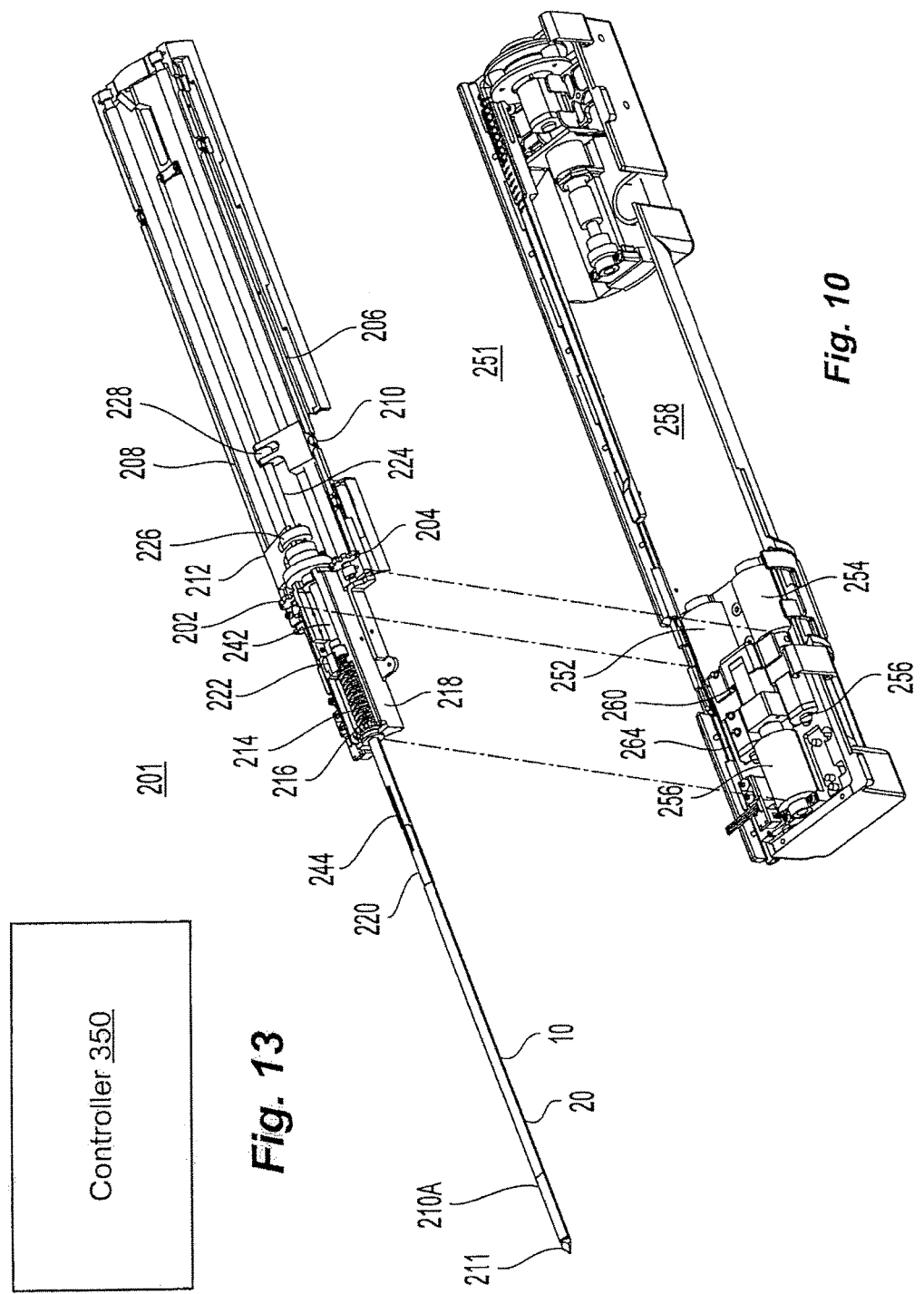

SINGLE-INSERTION, MULTIPLE SAMPLING BIOPSY DEVICE WITH LINEAR DRIVE

PRIORITY DATA AND INCORPORATION BY REFERENCE

This application is a continuation of U.S. patent application Ser. No. 13/592,062, filed Aug. 22, 2012, now U.S. Pat. No. 8,771,200, which is a divisional of U.S. patent application Ser. No. 11/997,403, filed Jul. 7, 2008, now U.S. Pat. No. 8,262,585, which is a U.S. national phase of International Application No. PCT/US2006/031325, filed Aug. 10, 2006, which claims benefit of priority to U.S. Provisional Patent Application Ser. No. 60/707,289 filed Aug. 10, 2005, each of which is incorporated by reference in its entirety.

FIELD OF THE INVENTION

This invention relates to a tissue biopsy sampling device.

BACKGROUND OF THE INVENTION

It is sometimes desirable or necessary to obtain specimens of tissue from humans and other animals, particularly in the diagnosis and treatment of patients with cancerous tumors, premalignant conditions, and other diseases or disorders. For example, when it is discovered that suspicious conditions exist, either by means of x-ray or ultrasound imaging in various tissues of the body, a physician usually performs a biopsy to determine if the cells at the suspected site are cancerous or benign.

A biopsy can be done either by an open or percutaneous technique. Open biopsy is an invasive procedure using a scalpel, by either a portion (incisional biopsy) being removed or the entire mass (excisional biopsy) is removed. Percutaneous biopsy is usually done with a needle-like instrument through a relatively small incision, and can be performed by fine needle aspiration (FNA) or through the taking of a core biopsy sample. In FNA biopsy, individual cells or clusters of cells are obtained for cytologic examination and can be prepared such as in a Papanicolaou smear. In a core biopsy, a core or fragment of the tissue is obtained for histologic examination.

Uncontaminated and intact tissue from the organ, lesion, or tumor is preferred by medical personnel in order to arrive at a definitive diagnosis regarding the patient's condition. In most cases only part of the tissue in question needs to be sampled. The portions of tissue extracted must be indicative of the organ, lesion, or tumor as a whole. Often, multiple tissue samples from various locations of the mass being sampled may be taken.

The percutaneous biopsy procedure can be performed utilizing various techniques and devices. One such biopsy device can include an inner stylet positioned inside an outer cannula, where the stylet is able to slide into and out of the cannula. The stylet can be a solid, pointed needle having a tissue sampling recess, and the cannula can be a hollow, open-ended needle having a sharp tip. The stylet and cannula can be manipulated cooperatively to capture a tissue sample in the sample recess. Such existing devices can be manually operated, semi-automated, and automated.

U.S. Pat. No. 6,485,436 shows a multiple sample biopsy needle with a hydraulic mechanism that circulates fluid from the tip of the needle back to a receiving basket or baskets. A revolver-type array of receiving chambers is disclosed.

U.S. Pat. No. 5,827,305 shows a tissue sampling needle that pushes a sample proximally using a saline wash. Samples remain spaced apart within the needle such that the sequence of their collection is preserved. Samples can also be removed from a port while the needle remains in place. No mechanical transport mechanisms or drives are disclosed.

U.S. Pat. No. 5,526,822 shows a transport system that uses a cannula and knock-out pin combined with a vacuum source to shuttle a tissue sample to a multiple-chamber cassette where it is knocked out. The cannula is then repositioned for another sample. The vacuum source is external. A revolving sample cassette is also shown. A vent opening in each sample cylinder of the cassette is provided to eject the fluid used to transport the tissue sample. A removable disposable needle-bearing cassette interfaces with rotary and linear drives by means of long gears and shuttles that cradle the gears. Cutters operate in rotary and linear fashion (a counter-rotating cutters embodiment is included) and the cannula can be rotated to orient the sample opening.

U.S. Pat. No. 6,017,316 shows a transport system similar to U.S. Pat. No. 5,827,822 in which a cutter transports with vacuum assist. Multiple sampling with single insertion is described but not automated multiple sample-handling. The details of a drive system are not disclosed.

U.S. Pat. No. 6,193,673 shows a needle with a durable part and a disposable part. An external cutting cannula rotates and advances axially to cut a sample. The tissue cutter is driven axially by a rack and pinion drive which are part of a durable component. A cradle connects the rack to the cutting cannula.

U.S. Pat. No. 5,944,673 describes a tissue extractor that rotates within a piercing needle to align with any one of multiple receiving ports while obstructing the remaining ports. The tissue sample is cut by advancing the cutter and removing by withdrawing the extractor. A vacuum holds the tissue sample in place during the removal of the tissue extractor from the cutter. The cutter rotates as it advances.

It is known to obtain a single sample with a single insertion. However, there are circumstances where there may be a need to obtain more than one sample. While the known biopsy needle can be re-inserted multiple times, such technique can cause pain and scarring of the body site.

It is known to leave a marker at the biopsied site. To do so, however, a physician or healthcare provider would typically need to withdraw the biopsy needle and insert a different device to leave a marker at the biopsied site. The additional step with the marker device concurrent with the tissue sampling may not allow the marker to be deposited at the actual biopsied site, which can lead to inaccurate post-biopsy diagnosis.

There is a need in the art for improved systems for performing multiple sample biopsies, particularly systems that are amenable to self-contained designs and improved techniques for sample extraction and handling. There is also a need for efficient and precise marker delivery with minimal trauma.

SUMMARY OF THE INVENTION

The present invention provides for exemplary embodiments of a single-insertion, multiple sampling biopsy device. The present invention also provides for exemplary embodiments of a single-insertion, multiple sampling device with integrated marker release.

In one aspect, a single-insertion, multiple sampling biopsy device that includes an outer cannula, a stylet, a sheath and a drive unit. The outer cannula extends along a longitudinal axis from a proximal end to a distal end, the outer cannula having a cutting end and a second through port proximal the cutting end. The stylet is disposed in the outer cannula and configured to translate along the longitudinal axis towards the distal and proximal ends in the outer cannula. The stylet has a second bulkhead being in fluid communication from a fluid source to the second bulkhead. The sheath is disposed between the outer cannula and the stylet, the sheath configured to translate along the longitudinal axis towards the distal and proximal ends. The sheath is disposed inside the outer cannula and configured to translate along the longitudinal axis towards the distal and proximal ends. The drive unit is coupled to the outer cannula, to transmit motive force to the cutting tip. The inner stylet and sheath translate relative to the outer cannula, and each other, via another drive unit.

In yet another aspect, a method of sampling biological tissue with a biopsy device is provided. The device has four elongated members that translate along a longitudinal axis between a distal end and a proximal end. The method comprising: capturing a biological sample in a chamber defined by two of the sheaths; and translating the two sheaths as a single unit through the interior first and fourth sheath to deliver the biological sample from the distal end to the proximal end.

In yet a further aspect, a method of transporting a tissue containing chamber with a biopsy device is provided. The biopsy device has four elongated members that translate along a longitudinal axis between a distal end and a proximal end. The method can be achieved by: (a) exposing a first aperture of a second sheath, the aperture having a chamber defined by a first and second bulkhead, and floor of the second elongate member; (b) providing a vacuum proximate the aperture; (c) enclosing the aperture of the second sheath with first elongate member; and (d) translating the chamber defined by the first, second, sheaths through a substantial portion of the outer cannula to expose the chamber in a proximal aperture formed through the outer cannula.

A preferred embodiment can include a single-insertion, multiple sampling biopsy device with an outer cannula extending along a longitudinal axis from a proximal end to a distal end, the outer cannula having a first port. A stylet may be provided and disposed in the outer cannula and configured to translate along the longitudinal axis towards the distal and proximal ends in the outer cannula, the stylet having a second port. A sheath may be disposed between the outer cannula and the stylet, the sheath configured to translate along the longitudinal axis towards the distal and proximal ends. A bulkhead may be disposed in the stylet and configured to translate with the stylet along the longitudinal axis towards the distal and proximal ends. A drive unit may be coupled to at least one of the outer cannula, stylet, and sheath to transmit motive force to at least one of the outer cannula, stylet, sheath to move at least the stylet relative to the outer cannula.

The bulkhead may include one or both of vacuum and pressurized fluid supply in fluid communication with a passage formed through the bulkhead. A fluid passage may be defined by the inner surface of the stylet and the outer surface of bulkhead, the fluid passage in fluid communication with one or more of a pressurized fluid supply and vacuum supply. The sheath may include a plurality of lands and openings that define a rack to engage with a pinion of the drive unit.

The sheath may include a selection mechanism to select between a first configuration where the sheath may be coupled to the stylet to move as a single unit and a second configuration where the stylet may be uncoupled from the sheath so that the sheath may be movable independently of the stylet.

The sheath may enclose the second port of the stylet to define a volume bounded by a rear bulkhead of the tip, the inner surface of the tip and the bulkhead. The stylet tip may include a marker disposed in the tip, the marker being ejected from the tip in an operative condition of the device. The stylet tip may include a marker mounted on the outer surface of the tip, the marker being separated from the tip in an operative condition of the device. The marker can be one or more of a hooked marker, helical marker and serrated edge marker. The marker can be an annular marker or a split-ring marker.

A preferred embodiment is also a method of sampling biological tissue with a biopsy device having three elongated members that translate along a longitudinal axis between a distal end and a proximal end. The method can be achieved by: capturing a biological sample in a chamber defined by two of the elongated members; translating the two elongated members as a single unit through the interior of a third elongated member to deliver the biological sample from the distal end to the proximal end.

A preferred embodiment is also a method of transporting a tissue-containing chamber with a biopsy device having four elongated members that extends along a longitudinal axis between a distal end and a proximal end, the method can be achieved by: exposing a first aperture of a first sheath and a second aperture of a second sheath, the second sheath having a chamber defined by a first bulkhead, a second bulkhead and a floor portion of the second sheath; providing a vacuum proximate the second aperture; enclosing the second aperture of the second sheath with a third sheath; and translating the chamber defined by the second and third sheaths through a substantial portion of a fourth sheath to expose the chamber in a third aperture formed through the fourth sheath.

A preferred embodiment also provides a single-insertion multiple sample biopsy device, in which an outer cannula extends along a longitudinal axis from a proximal end to a distal end. The outer cannula has a cutting distal end and a side port arranged proximal to the distal end. A trochar tip is supported by twin longitudinal members that remains stationary relative to the outer cannula and the two internal retracting longitudinal members. There is a first sheath within the outer cannula, with a distal beveled end. The sheath is configured to translate along a longitudinal axis between the distal and proximal ends. There is a second sheath within the outer cannula configured to translate along a longitudinal axis between the distal and proximal ends. The sheath has distal and proximal bulkheads that form a tissue accepting port. The proximal bulkhead also forms a fluid passage in communication with the proximal end. A drive unit translates and revolves the outer cannula relative to the three inner members. Another drive unit translates the first and second sheaths relative to the trocar tip assembly and outer cannula where the two sheaths can transpose relative to each other in a timed relationship.

A preferred embodiment also provides a single-insertion, biopsy device that includes a cannula has a proximal end, a distal end, an extraction port at the distal end and a recovery position at the proximal end. First and second elongate elements have distal ends that are movable between the extraction port of the cannula and the recovery position of the cannula. The first and second elongate elements are also movable with respect to each other to define extraction and closed configurations. In the open configuration, the first and second elongate element distal ends define a recess with an access. The access faces the extraction port. In the closed configuration, the first and second elongate element distal ends are mutually opposite to surround a volume. A drive unit coupled to the first and second elongate elements configures them between the open configuration and the closed configurations and transfers the first and second elongate element distal ends from the extraction port to the recovery position.

The drive unit may transfer the first and second elongate element distal ends to the recovery position while the first and second elongate elements are in the closed configuration. The cannula may have a recovery port at the recovery position and the drive unit configures the first and second elongate elements into the open configuration after transferring their distal ends to the recovery position such that the volume may be open to the recovery port.

According to an embodiment, the invention is a single-insertion, multiple sampling biopsy device having a sheath extending along a longitudinal axis from a proximal end to a distal end. The sheath has a sample recess space within it. The sheath is selectively configurable to open and close the sample recess space. The sheath has a movable bulkhead within it which is located at a distal end of the sample recess. The sheath has a sample recovery port located proximal of the sample acquisition port. A drive unit is provided which couples to the first bulkhead to move it from the distal end of the sheath to the sample recovery port to transport the sample received in the sample recess to the sample recovery port. According to this embodiment, the transport system transports multiple samples in this manner under user control without removing the sheath from the host.

Preferably, a second bulkhead is located on a side of the sample recess opposite the first bulkhead. The second bulkhead preferably has a port connected to a source of vacuum and/or pressurized fluid. Preferably, the second bulkhead is connected to the drive unit to move with the first bulkhead. Preferably, also, the sheath contains first and second elements that move independently in distal and proximal directions relative to the sheath. Here, the directions are collinear with an axis of the sheath, and the first and second elements form respective parts of a cylindrical conduit connected at a proximal end to a vacuum source and connected at a distal end to the sample recess.

Preferably, the sheath is directly adjacent the first and second independently movable elements where the sheath holds the first and second independently movable elements in alignment. In an embodiment, the first and second independently movable elements are hemicylinders.

Also, preferably, there is a selective engagement device and the sheath contains first and second elements that move independently in distal and proximal directions, where the directions are collinear with an axis of the sheath. In this embodiment, the selective engagement device interconnects the first and second elements, the drive unit being connected to move one of the first and second elements and to move the other of the first and second elements selectively depending on whether the engagement device is engaged to interconnect the first and second elements.

In an embodiment, the first bulkhead is connected to one of the first and second elements. In another embodiment, the sheath has a selection mechanism to select between a first configuration where the sheath is coupled to the stylet to move as a single unit and a second configuration where the stylet is uncoupled from the sheath so that the sheath is movable independently of the stylet.

In all the above embodiments, a cutting tip extends distally of a distal terminus of the sheath where the cutting tip is connected to one of the first and second elements.

In another variation of the base embodiment, a selective engagement device is provided. The sheath contains first, second, and third elements, the first and second of which move independently in distal and proximal directions. The directions are collinear with an axis of the sheath and the third element is parallel and substantially coextensive with the first and second elements along an axis of the sheath. In this case, the third element has a cutting tip extending distally of a distal terminus of the sheath.

Preferably, the tip includes a marker mounted on the outer surface of the tip, the marker being separated from the tip in an operative condition of the device. The marker is preferably one or more of a hooked marker, helical marker and serrated edge marker.

According to an embodiment, the invention is a method of sampling biological tissue with a biopsy device having first and second elongate members that translate within a third elongate along a longitudinal axis between a distal end and a proximal end, the method can be achieved by: capturing a biological sample in a chamber defined between the first and second elongated members, translating the first and second elongate members. According to another embodiment, the invention is a single unit through the interior of the third elongate member to deliver the biological sample from the distal end of the third elongate member to the proximal end of the third elongate member. Preferably, the method includes translating the first and second elongated members through the third elongated member in a reverse direction to repeat the capture and translation of another sample. Also preferably, the method includes cutting the sample from a host by translating the third elongate member relative to the first and second elongate members, the third elongate member having a cutting edge at a distal end thereof that effects the cutting.

According to an embodiment, the invention is a method of transporting a tissue-containing chamber with a biopsy device having four elongated members that extends along a longitudinal axis between a distal end and a proximal end, the method can be achieved by: exposing a first aperture of a first sheath and a second aperture of a second sheath, the second sheath having a chamber defined by a first bulkhead, a second bulkhead and a floor portion of the second sheath, providing a vacuum proximate the second aperture, enclosing the second aperture of the second sheath with a third sheath, and translating the chamber defined by the second and third sheaths through a substantial portion of a fourth sheath to expose the chamber in a third aperture formed through the fourth sheath.

According to another embodiment, the invention is a single-insertion, multiple sampling biopsy device with an outer cannula extending along a longitudinal axis from a proximal end to a distal end, the outer cannula having a cutting distal end and a side port arranged proximal of the distal end. A cutting tip supported by twin longitudinal members remains stationary relative to the outer cannula, and the two internal retracting longitudinal members. A first sheath within the outer cannula, with a distal beveled end, translates in the distal and proximal directions. A second sheath within the outer cannula is configured to translate along a longitudinal axis between the distal and proximal ends. The sheath has distal and proximal bulkheads that form a tissue accepting recess, the proximal bulkhead also forming a fluid passage in communication with the proximal end. A drive unit translates and revolve the outer cannula relative to the three inner members. The drive unit translates the first and second sheaths relative to the cutting tip and outer cannula where the two sheaths can translate relative to each other in a predetermined relationship.

According to another embodiment, the invention is a single-insertion, biopsy device with a cannula that has a proximal end, a distal end, an extraction position at the distal end and a recovery opening at the proximal end. There are first and second elongate elements with distal ends that are movable between the extraction position of the cannula and the recovery opening of the cannula. The first and second elongate elements are also movable with respect to each other to define extraction and closed configurations. In the extraction configuration, the first and second elongate element distal ends define a recess at the extraction position. This recess has an access. In the closed configuration, the first and second elongate element distal ends are mutually opposite to surround a volume. A drive unit coupled to the first and second elongate elements configures them between the open configuration and the closed configuration. The drive unit also transfers the first and second elongate element distal ends from the extraction position to the recovery opening. Preferably, the drive unit transfers the first and second elongate element distal ends to the recovery opening after placing the first and second elongate elements in the closed configuration. Also, preferably, the drive unit configures the first and second elongate elements into the open configuration after transferring their distal ends to the recovery opening. The cannula preferably has a cutting edge at its distal end and the drive unit moves the cannula to place the cutting edge over the recess at the extraction position.

In another embodiment, the invention is a method of taking a biopsy tissue sample including receiving a sample in a stylet, held within a cutting cannula, while the stylet and cutting cannula are inserted in a host, and moving the stylet, relative to the cutting cannula, repeatedly from a sample receiving position to a sample recovery position, while maintaining the cutting cannula in place within the host. Preferably, the stylet has a cutting tip affixed thereto such that the cutting tip is moved with the stylet. Also, preferably, the receiving operation includes receiving the sample adjacent a bulkhead affixed to the stylet so that the bulkhead pushes the sample as the stylet is moved.

In a variation of the embodiment, the method includes applying a vacuum to the stylet where the sample is received and cutting the sample free of the host. Preferably, the method also includes extending a cover over the sample before moving the stylet relative to the cutting cannula. The extending can include axially moving an elongate member relative to the stylet and the cutting cannula, the elongate member forming a portion of a cylinder with a major portion of the stylet, the cylinder being coaxially arranged within the cutting cannula. In another variation, the method includes deploying a tissue marker from a tip of the stylet.

According to another embodiment, the invention is a method of taking a biopsy tissue sample. The method includes receiving a sample in a stylet, held within a cutting cannula, while the stylet and cutting cannula are inserted in a host; and extending a cover over the sample and moving the stylet relative to the cutting cannula from a sample receiving position to a sample recovery position, while maintaining the cutting cannula in place within the host.

Preferably, the receiving and extending operations are done repeatedly to recover multiple samples. The stylet preferably has a cutting tip affixed thereto such that the cutting tip is moved with the stylet. Preferably the receiving operation includes receiving the sample adjacent a bulkhead affixed to the stylet, the bulkhead pushing the sample as the stylet is moved. Preferably, a vacuum is applied to the stylet where the sample is received and cutting the sample free of the host. The extending preferably includes axially moving an elongate member relative to the stylet and the cutting cannula, the elongate member forming a portion of a cylinder with a major portion of the stylet, the cylinder being coaxially arranged within the cutting cannula. In a refined embodiment, the method includes deploying a tissue marker from a tip of the stylet.

According to another embodiment, the invention is a biopsy device, with a stylet that has a sample recess at a distal end and a cannula with sample acquisition port and a sample recovery port. The stylet is movable within the cannula to move its sample recess from the sample acquisition port to the sample recovery port. A cover member is movable relative to the stylet to cover the sample recess selectively. A transport mechanism is connected to move the stylet and cover. The transport mechanism covers the sample recess when a sample is received thereat and moving the sample recess such that a sample in the sample recess is prevented from rubbing against the cannula. The transport mechanism moves the cover to uncover the sample recess to recover the sample when the sample is moved to the recovery port.

Preferably, the sample recess is only partially uncovered at the recovery port while the transport mechanism conveys fluid under pressure to the sample recess to eject the sample. Also preferably, the stylet has a cutting tip affixed thereto such that the cutting tip is moved with the stylet. The transport mechanism preferably creates a vacuum in the stylet sample recess to urge tissue into it and moves the cannula relative to the sample recess to cut a sample.

According to another embodiment, the invention is a method of taking a biopsy tissue sample. The method includes covering a sample with a cover member in a sample recess while moving the recess within a cannula, to prevent the sample from frictionally engaging the cannula and partially uncovering the sample recess at a sample recovery position while injecting fluid under pressure to remove the sample from the sample recess.

In all of the above devices, a vacuum source and a power source may be provided in a self-contained hand-held biopsy device. In all of the methods, a biopsy unit may contain a controller programmed to execute the methods automatically or contingent on consecutive command being entered through the biopsy device.

BRIEF DESCRIPTION OF THE DRAWINGS

The accompanying drawings, which are incorporated herein and constitute part of this specification, illustrate presently preferred exemplary embodiments of the invention, and, together with the general description given above and the detailed description given below, serve to explain features of the invention.

FIGS. 2A-2G illustrate an exemplary embodiment of ancillary components for the biopsy cutter and transport assembly of FIG. 1.

FIGS. 3A-3H and 3J-3M illustrate a sequence of biopsy tissue extraction of the device of FIG. 2A.

FIGS. 4A-4H illustrate a sequence of biopsy tissue extraction using a variation of the device of FIG. 2A.

FIGS. 5A-5H, 5J and 5K illustrate a sequence of biopsy tissue extraction using yet another variation of the device of FIG. 1.

FIGS. 6A-6G illustrate an integrated biopsy marking system for each of the devices of FIGS. 1-5.

FIGS. 8A1, 8A2, 8A3, 8B, and 8C illustrate a further integrated biopsy marking system for each of the devices of FIGS. 1-5.

FIGS. 9A and 9B illustrate yet another integrated biopsy marking system for each of the devices of FIGS. 1-5.

FIGS. 10 and 11 illustrate components of a drive mechanism for a biopsy needle having a disposable part and a durable part which mate to create an operable device.

FIG. 13 illustrates a controller.

DETAILED DESCRIPTION OF THE PREFERRED EXEMPLARY EMBODIMENTS

Figure 1:
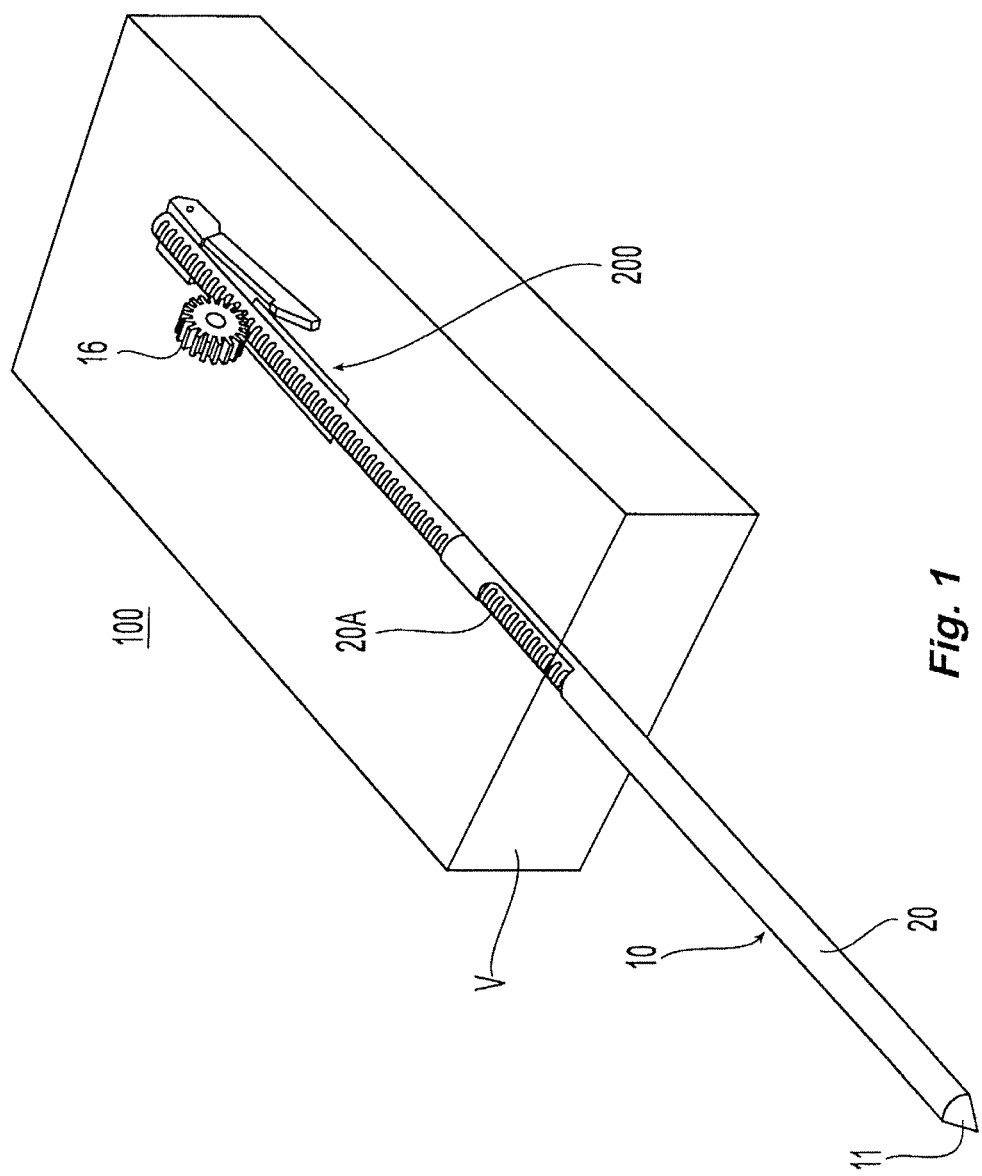
FIG. 1 illustrates a perspective view of a biopsy cutter and transport subassembly according to one exemplary embodiment of the present invention.
Figure 2F:
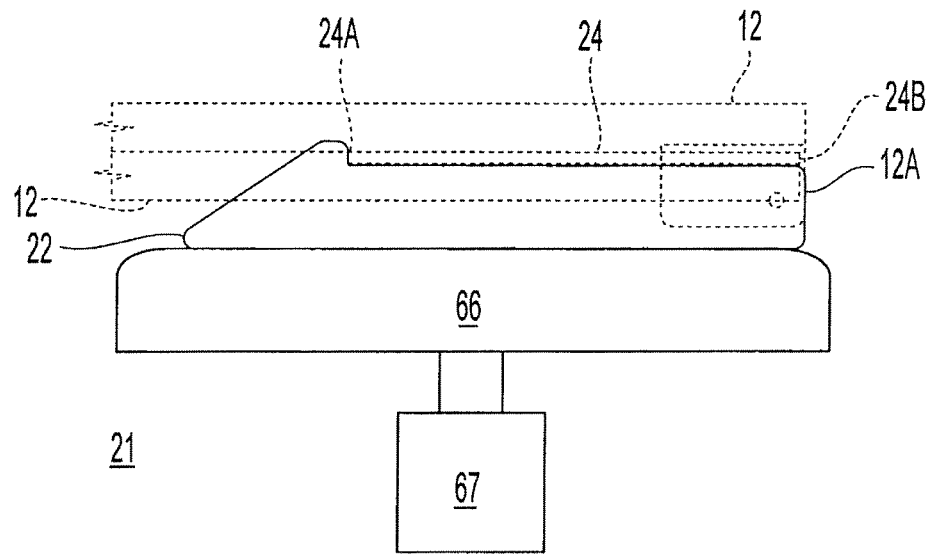
Figure 2G:
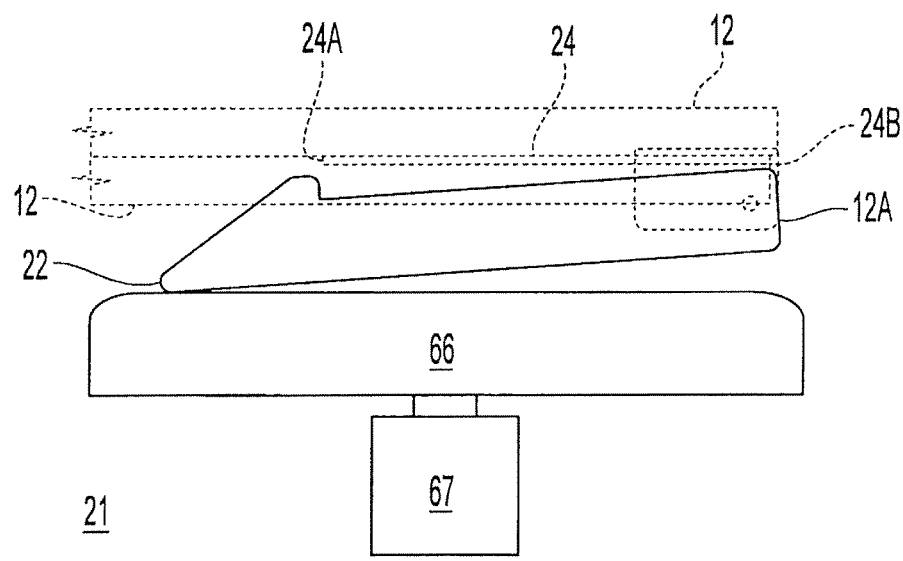

FIGS. 1-12B illustrate the preferred exemplary embodiments which utilize the same reference numeral to indicate generally similar components. In particular, referring to FIG. 1 is a perspective view a single-insertion, multiple samples biopsy device 100 provided with a transport subassembly 200 and a biopsy needle 101. Visible in FIG. 1 is a cylindrical outer cutting cannula 20 that has a proximal sample recovery port 20A which provides access to a channel 10B defined between a sheath 12 and a stylet 10. Cutting cannula 20 has a distal sample acquisition port 20B (see FIGS. 3A and 3D). The sheath 12 and the stylet 10 are shaped like half-cylinders arranged in mirror-image fashion to surround the channel 10B. The sheath 12 and the stylet 10 are surrounded, and held in place, by the cutting cannula 20.

Referring now also to FIGS. 2A through 4H, the transport subassembly 200 drives the stylet 10 and the sheath 12. The stylet 10 carries a stylet tip 11, which is preferably shaped for insertion into a host, for example, a trocar. There is a first bulkhead 11A at the rear end of the stylet tip 11. A second bulkhead 14A or 14B, which may be a cylindrical element with a hole (14A) or a D-shaped element (14B) acts as a mechanical barrier, but allows fluid to pass through it. The first bulkhead 11A and second bulkhead 14A or 14B together define a sample acquisition recess 10A between them. The cutting cannula 20 extends over a substantial length of the stylet 10, covering the sample acquisition recess 10A when fully extended toward the distal end of the stylet 10.

Ancillary components of the device 100 such as respective saline and vacuum reservoirs, motor drive, reduction gears, switches and sensors (not shown) can be coupled to the sample recess 10A through the transport subassembly 200. The sheath 12 can be provided with a fluid conduit 110 (shown in FIGS. 3G to 3L) to convey air through a pressurized or negative pressure (i.e., vacuum) source. In addition, or in the alternative, the second bulkhead 14A or 14B can be in fluid communication with a bio-compatible fluid such as, for example, saline. A passage 14C (shown in FIG. 4E and corresponding to the second bulkhead 14A embodiment of FIG. 4A) or 14D (shown in FIG. 3A and corresponding to the second bulkhead embodiment 14B of FIGS. 4A through 4H) opens to the sample acquisition recess 10A and allows a fluid, such as air or saline, to pass through the passage 14C or 14D into the sample acquisition recess 10A or 14C or 14D. Alternatively air or fluid can be pumped out of the sample acquisition recess 10A through the passage 14C or 14D. Additional passages can be provided in the second bulkhead with respective conduits, similar to conduit 110, provided to connect them to a fluid conveyance mechanism.

Focusing for now on FIGS. 3G TO 3L, the conduit 110 may be a flexible polymer tube, such as of polyvinyl chloride (PVC) commonly used in medical equipment. In the embodiment, the conduit 110 terminates in a boss 99 that fits snugly in the channel 10B and is attached to the stylet 10. In an embodiment in which the sheath 12 has a rack portion 12B with openings cutting through the sheath, the boss 99 is preferably located distally of that rack portion 12B so that the channel 10B, defined by the sheath 12 and stylet 10, is substantially sealed between the boss 99 and the bulkhead 14A. The bulkhead 14A is similarly attached to the stylet. Suction applied to the conduit 110 draws air from the channel 10B out through the opening 14D and out from the sample acquisition recess 10A. Air or other fluids can be conveyed in the opposite direction, under pressure, through the conduit 110 and into the sample acquisition recess 10A.

In alternative embodiments, the bulkhead 14A can be replaced in this embodiment by the D-shaped bulkhead 14B. The bulkhead 14A and the boss 99 can also be replaced by an extension of the conduit 110 that runs right up to the sample acquisition recess 10A forming a bulkhead with its distal end. The boss 99 can be located proximally of a rack portion 12C without permitting a leak if the rack portion 12C is formed by a closed toothed pattern on the sheath 12 as illustrated in FIG. 3M.

In the transport subassembly 200, the rack portion 12B, 12C, both of which are indicated generically by reference numeral 18, engages a pinion 16 proximate the sample recovery port 20A. Referring to FIGS. 2A through 2E, the use of the pinion 16 and rack 18 with the latching mechanism 21 allows both the sheath element 12 and the stylet 10 to be moved simultaneously when the latching mechanism 21 is engaged. When the latching mechanism 21 is disengaged, the sheath element 12 moves relative to the stylet 10 as the pinion 16 rotates. As shown in FIGS. 2A to 2E, the sheath element 12 has a hinge 12C with at least one pivoting member 22 with a distally-located shoulder 12A and a proximally-located tab 12B. The pivoting member 22 is moved into an engaged position (up) to connect the stylet 10 to the sheath element 12 and into a disengaged position (down) to disconnect the stylet 10, thereby allowing the sheath element to move relative to the stylet.

Referring to FIGS. 2A and 2B, the cutting cannula 20 can be retracted (FIG. 2A) and advanced (FIG. 2B) by a suitable mechanism such as, for example, the worm drive assembly described in U.S. Patent Application Publication No. 2005/0165328 published on Jul. 28, 2005, which is incorporated by reference in its entirety herein to this application.

Referring to FIGS. 2C through 2G, the pivoting member 22 can be moved into engaged and disengaged positions by any suitable actuator, for example a solenoid actuator 67 connected to a glide 66 both of which are attached to a housing. When the glide 66 is in an engagement position, it pushes the pivoting member 22 into the engaged position and holds it while permitting the pivoting member 22 to move with the sheath element 12 by allowing the pivoting member 22 to slide on it. Preferably, the glide 66 has a low friction surface, such as Nylon.

Referring to FIGS. 3G to 3L, the outer cutting cannula 20 is shown in an extended position for insertion into a host from which a sample is to be obtained. The sheath element 12 is also in the extended position covering the sample acquisition recess 10A. A vacuum is applied through the conduit 110 causing a vacuum to be generated in the sample acquisition recess 10A. The cutting cannula 20 and the sheath element 12 are then retracted as shown in FIG. 3H. For this operation, the sheath element 12 is disconnected from the stylet 10 by disengaging the latch mechanism 22 so that the stylet can remain in place as the sheath element 12 is retracted. The sheath element 12 may be retracted before the cutting cannula 20, or simultaneously with the cutting cannula 20. When the sample acquisition recess 10A is exposed to the host 103, the vacuum causes tissue from the host 103 to be drawn into the sample acquisition recess 10A. External pressure may also be applied at this point, for example manually by the user. The cutting cannula 20 is then extended as shown in FIG. 3J, severing a tissue sample BSM from the host 103. Next, as shown in FIG. 3K, the sheath element 12 is advanced so that its distal end covers the sample acquisition recess 10A. The latch mechanism 21 is then engaged locking the sheath element 12 to the stylet 10 so that when the sheath element is again retracted, as shown in FIG. 3L, the stylet 10 is also retracted. The cutting cannula 20 stays in position relative to the host 103.

Note that the extension of the sheath element 12 so that its distal end covers the sample acquisition recess 10A is a beneficial feature of the embodiments here and elsewhere in the present disclosure. By covering the sample acquisition recess 10A, the sample is prevented from frictionally engaging the cutting cannula as the stylet and cover are moved proximally. This helps to ensure sample integrity. Also, the sheath element helps to reduce the outlet area for ejection of the sample as discussed elsewhere.

FIGS. 3A to 3F show the biopsy needle operations just described in a perspective view. In FIG. 3A, the cutting cannula 20 is retracted, exposing the sample acquisition recess 10A within the stylet 10. The sample acquisition recess 10A has an internal volume defined by the second bulkhead 14A, the first bulkhead 11A, and the inside surface of the stylet 10 and cutting cannula 20 (when closed). The vacuum is caused by sucking air through the passages 14D (or 14C in the alternative embodiment) causing the biological tissue sample BSM to be deposited in the sample acquisition recess 10A, shown here in FIG. 3B.

For a 14 gauge stylet or needle, the internal volume is sufficient to capture a mass of at least 50 milligrams of biological tissues, e.g., turkey breast tissues used in testing. For a 10 gauge stylet 10, the internal volume is sufficient to capture a mass of at least 150 milligrams or more of biological tissues, e.g., turkey breast tissues. The length of the stylet 10 can be of any suitable lengths, such as, for example, about 250 to about 300 millimeters. The volume V of the housing containing all of the components of the device 100 is preferably 500 cubic centimeters or less and preferably about 320 cubic centimeters with particularly preferable dimensions of about 40 millimeters by about 40 millimeters and about 200 millimeters. As used herein, the term "about" or "approximately" for any numerical values indicates a suitable dimensional tolerance that allows the part or collection of components to function for its intended purpose as a biopsy cutter, biopsy system or the combination of both the system and cutter.

Once the cutting cannula 20 extends proximate the rear bulkhead 11A of the stylet tip 11 to sever the biological tissue BSM, as shown in FIG. 3B, the sheath element 12 can be extended distally to completely surround the tissue sample (FIG. 3C). The cutting action by the cutting cannula 20 can be by translation, rotation, translation and rotation or a combination of these movements along with back and forth axial movements of the cutting cannula 20 as part of the cutting strategy. FIG. 3E shows the cutting cannula 20 in its preferred stationary position with the stylet 10, stylet tip 11, and the sheath element 12 retracted. The sample acquisition recess 10A is retracted until it is aligned with the sample recovery port 20A where bio-compatible liquid 26, fluid 28, or air can be used to expel the sample BSM from the sample recovery port 20A, shown here in FIG. 3F, into a receptacle (not shown). The device 100 is then ready to move towards the initial position in FIG. 3A to take another sample.

An alternative device to obtain a tissue sample or multiple tissue samples can be seen with reference to FIGS. 4A-4H. In this embodiment, the second bulkhead 14B is not provided with a hollow fluid passage 14D. Instead, the second bulkhead 14B is formed with a D-shaped cross-section so that a fluid passage 14C can be formed between the inner surface of the stylet 10 and the longitudinal outer surface of the second bulkhead 14B. While it is preferable that the second bulkhead 14B is fixed in relation to the stylet 10, the second bulkhead 14B can be configured to move for other purposes, such as, for example, adjusting the sampling volume. As shown in FIG. 4A, vacuum can be provided via passage 14C to draw the biological tissue into the sample acquisition recess 10A. The cutting cannula 20 can be translated or both translated and rotated to sever the tissue sample BSM from the main mass of biological tissue M (FIG. 4B). The sheath 12 can be extended via the rack and pinion mechanism to enclose the biological tissue BSM for transport towards the sample recovery port 20A (FIG. 4C) while maintaining the outer cannula generally at a fixed location (FIG. 4D). It should be noted that a volume to contain the sample is defined by the bulkhead 11A of the tip, the inner surface 11B of the stylet tip 11, the inner surface of the sheath 12 and the second bulkhead 14B.

Referring to FIGS. 5A-5K, in another alternative embodiment, the stylet tip 11 of an alternate stylet 13 is stationary while the sheath 12 with a distal beveled end 12D and stylet 10 are translated along at least one stylet rail 13A. This embodiment serves to reduce the possibility of biological tissue being drawn into the interior of the cutting cannula 20 as would be the tendency in the embodiment of FIG. 3D as the stylet 10 is retracted proximally. In this embodiment, the second bulkhead 15 is provided with first port 15A and the cutting cannula 20 is provided, as in the previous embodiments, with the sample recovery port 20A. The stylet tip 11 is attached to a stylet rail 13A which remains fixed relative to a drive system (not shown here), while the cutting cannula 20, sheath element 12, and stylet 13 move relative to it. The drive system may be similar to transport subassembly 200 described above. The stylet 13, the cutting cannula 20, and the sheath element 12 move as in the previous embodiment, but the stylet rail 13A remains fixed to keep the stylet tip 11 in a fixed location relative to the host.

The sampling sequence is as follows. In FIG. 5A, the cutting cannula 20 is translated or rotated or a combination of both proximally to expose the port 15A of the stylet 10 and bulkhead 15. Vacuum can be provided through passage 15B to draw the tissue sample into the port 15A. To separate a tissue sample from the host, the outer cannula is moved distally as shown in FIG. 5B. Thereafter, the sheath 12 is advanced over the port 15A to enclose the sample and the sample transported along stylet rails 13A towards the sample recovery port 20A, shown here in FIGS. 5C, 5D, and 5E. The sequence of tissue sampling is also shown in a side view in FIG. 5F for clarity. In the preferred embodiments, there are two rails but three, four or more rails can be used as needed for structural rigidity. FIG. 5K shows the section A-A indicated in FIG. 5A for clarification of the relationship between the elements discussed above.

The examples shown in the illustrations and described in detail above can be integrated with one or more of four exemplary marking systems. In particular, each of four marking systems can be integrated with each of the examples described above to provide for at least eight different integrated biopsy cutter and marking systems. For clarity, only the four marking systems will be described and shown below. However, it should be clear that each marking system can be combined with another of the biopsy cutter systems as appropriate to arrive at a suitable combination of biopsy sampling device and integrated marker.

In the foregoing embodiments, the sheath element 12 and stylet 10, 13, and stylet rail 13A can be made of materials and thicknesses with insufficient strength to be entirely self-supporting. This is because the cutting cannula 20 closely surrounds and helps to support these elements. So the cutting cannula 20 can help to support these elements. Also, these elements also act together, held in close alignment by the cutting cannula 20 so that they can better resist any tendency to be twisted by the cutting cannula 20 as it rotates.

Referring to FIGS. 6A-6G, a marking system utilizing a hook type marker 40 (i.e., a "harpoon") to prevent migration of the marker 40 once it has been deployed, is shown. The hook type marker 40 with hook 42 or 44 can be deployed in sequence or simultaneously with the sampling of biopsy tissues with the various technologies described in relation to FIGS. 1-5 above. As shown in FIGS. 6A and 6E, a member (e.g., an internal D-Rod 14A, 14B, or the cutting cannula 20) can be used to eject a marker 40 stored in the stylet tip 11. In the exemplary embodiment of FIGS. 6A-6G, a second bulkhead 14B is provided with a cut-out portion 14B1 having a ramp 14B2 formed on a distal end of the rod 14B. The ramp 14B2 can be used (depending on whether the cutting cannula 20 or rod 14B is axially translated only, rotated only or a combination of axial translation and rotation) to ensure that the marker 40 is deposited sufficiently near the tissue sampling site. Various marker configurations can be utilized. For example, as shown in FIG. 6D, a marker with wire like hooks 40, square sectioned hook 40B, or marker with serrated edges 40C can be used in this system.

Figure 7B:
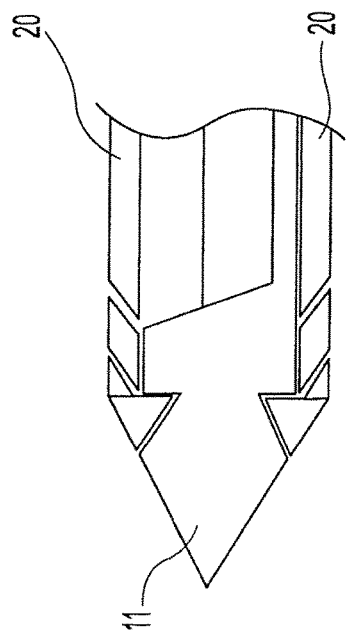
FIGS. 7A-7D illustrate another integrated biopsy marking system for the devices of FIGS. 1-5.
Figure 7D:
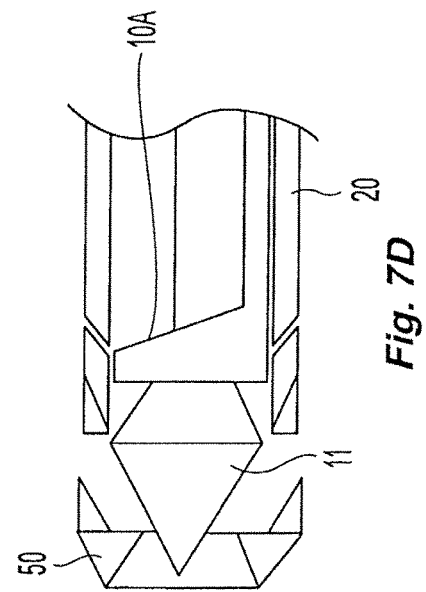
Figure 7A:
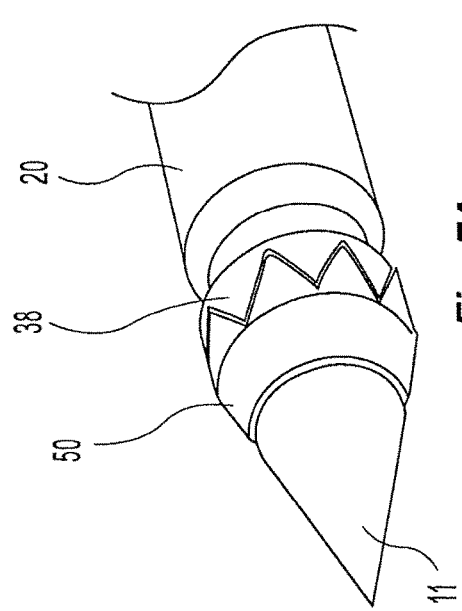
Figure 7C:
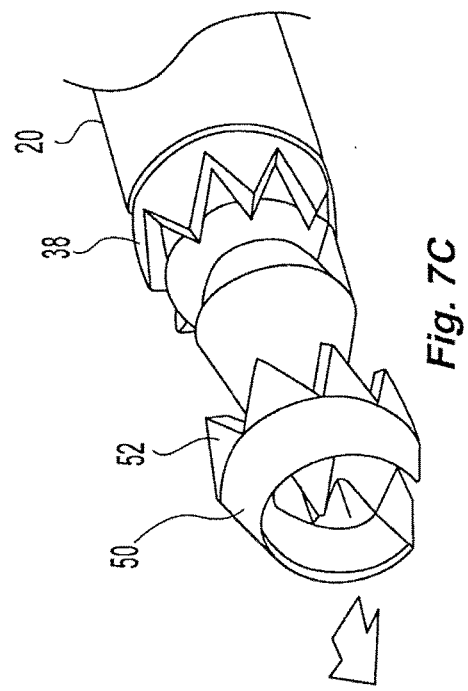

Referring FIGS. 7A-7D, a marking system utilizing a split ring marker 50 can be utilized with various biopsy techniques described above in relation to FIGS. 1-5. In FIGS. 7A and 7B, the split-ring marker 50 can be mounted to the stylet 10 via a suitable technique such as, for example, crimping, swaging or semi-permanent bonding. Optionally, an intermediate member 38 that forms a seal with the cannula or cutting cannula 20 can be provided to maintain a generally constant outer diameter of the cutting cannula 20 without an abrupt transition to the stylet tip 11. Referring to FIGS. 7C and 7D, the split-ring marker 50 can be deployed by itself, simultaneously with the sampling of the tissue, prior to sampling or subsequent to the sampling. As shown in FIGS. 7C and 7D, the stylet tip 11 can be actuated proximally towards the user to force the split-ring marker 50 to detach from the stylet tip 11. Alternatively, the cutting cannula 20 can be actuated distally away from the user to force the split-ring marker 50 to separate from the stylet tip 11.

Referring to FIGS. 8A1, 8A2, 8A3, 8B, and 8C, a marking system using a blossom-type marker 60 can be utilized with various biopsy techniques described above in relation to FIGS. 1 and 2. As shown in FIGS. 8A1-8A3, in perspective, and in 8B and 8C in section, the blossom marker 60 is mounted on a specially configured stylet tip 111 (FIG. 6C), which has grooves 112 and ramps 114 disposed about a longitudinal axis of the stylet tip 111. The blossom marker 60 can be mounted by a suitable technique, such as, for example, crimping, swaging, or casting onto the specially configured stylet tip 111. The cutting cannula 20 can be moved distally away from the user to force the blossom marker 60 to be separated from the stylet tip 110. As the marker 60 is separated from the stylet tip 111, the ramps 114 on the stylet tip 111 force the sectioned tips 62A-62E to blossom, thereby forming hooks 64A-64E. Alternatively, the stylet tip 111 can be moved proximally towards the user so that the marker is deployed by pushing against the cutting cannula 20.

Referring to FIGS. 9A and 9B, another marking system is shown which uses a spiral-type marker 70 in conjunction with various biopsy systems described above in relation to FIGS. 1-5. As shown in FIG. 9A, a coiled marker wire 70 can be disposed in an interior hollow section 113 of the stylet tip 11. A suitable deployment mechanism can be used to eject the coiled marker wire out of its storage space in the stylet tip 11. The deployment mechanism can be a suitable mechanism, such as, for example, a linear-to-rotary motion converter that converts a linear motion into a rotary motion to rotatably expel the marker. For example, the shuttle 14A can have a notch at its distal end that engages with the marker wire 70 and rotates it.

The materials suitable for use as part of each marker can be, for example, stainless steel, gold, titanium, platinum, tantalum, barium sulfate, biodegradable iron or shape memory polymer or metal alloy such as Nitinol. It is noted that Nitinol is radio-opaque, ultrasonically opaque and MRI compatible and therefore would be preferred by itself or in combination with other materials described herein and as known to those skilled in the art. Further, the markers can be of any suitable size so that it can be fitted onto a 7, 8, 9, 10, 11, 12, 14, or 16 gauge needle.

Although the markers have been shown as a single deployment marker, some of the embodiments disclosed herein can be utilized in a multiple deployment aspect. For example, the stylet tip 11 can be configured to store a plurality of harpoon markers 40; the stylet 10 can be mounted with a longitudinal series of split-ring markers 50; the stylet tip 11 can be configured with a cutter so that multiple helical markers 70 can be deployed.

Figure 11:
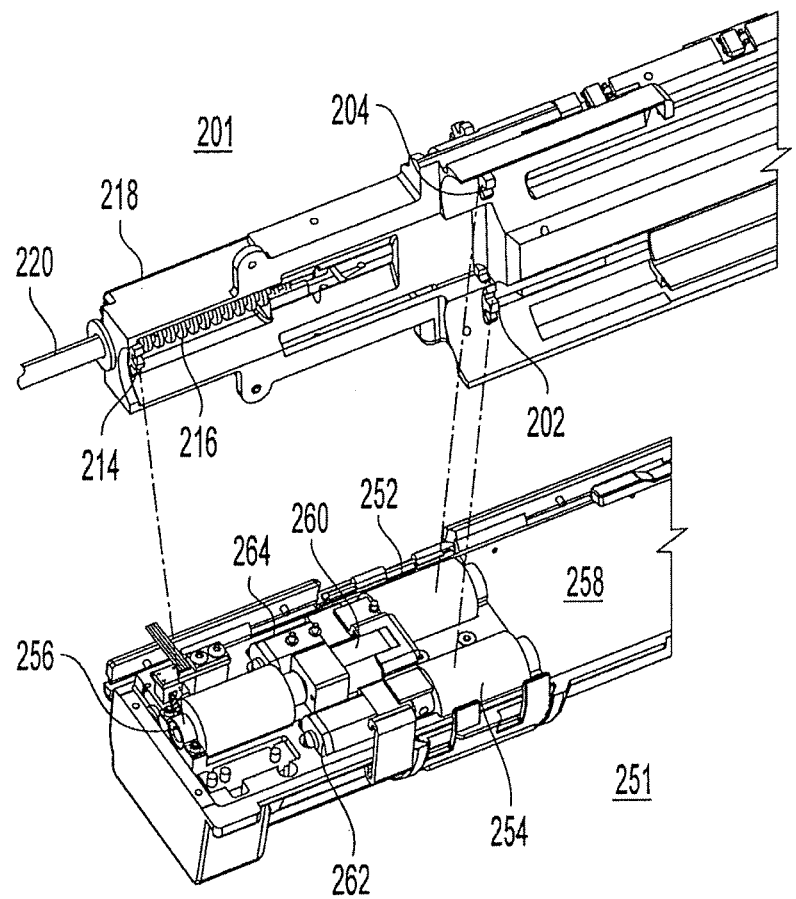

FIGS. 10 and 11 show an alternative embodiment of a drive system for driving the cutting cannula 20, the sheath 12 and the stylet 10 of the above embodiments as well as other embodiments. The assembly 201 and 251 consists of a disposable component 201 carrying a cutting cannula 20, a stylet 10 within the cutting cannula 20, which carries a trocar tip 211. The stylet 10 has a port 210A. The assembly 201 and 251 is illustrated such that only the drive components are shown, and a durable component 251. Although not shown in the figure, the disposable component 201 may include components such as a sample chamber, fluid circuits for conveying saline and a vacuum, and other elements which may be identified with the above descriptions of embodiments of biopsy devices and their operation.

According to one embodiment, a cutter extension 220 forms an axial extension to the cutting cannula 20 and surrounds an upper half-pipe 242 and a lower half-pipe 224. The upper half-pipe is an axial extension of sheath 12 and the lower half-pipe is an axial extension of the stylet 10. The three: cutter extension 220, lower half-pipe 224 and upper half-pipe 424 are independently movable, in an axial direction, with respect to each other. In this and other embodiments, the half-pipes can be replaced with other partial cylindrical or prism sections capable of providing mating sections. For example, a ¾ pipe could be made with a ¼ pipe. In addition, the longitudinal members could overlap such that the mating pairs define a complete (circular) section but the sum of the circumferential extent of their cross-sections can be greater than a full circle.

The upper half-pipe 224 and the lower half-pipe 242 are driven by respective lead screws 206 and 208, which rotate in the chassis 218; the lead screw 206 driving the upper half-pipe 224 and the lead screw 208 driving the lower half-pipe 242. The lead screws 206 and 208 thread into traveling carriages 210 and 212, respectively.

The carriage 210 engages a journal 228 affixed to the end of upper half-pipe 224 so that when the lead screw 206 turns, the carriage 210 moves axially causing the upper half-pipe 224 to move axially with it. Similarly, the carriage 212 engages a journal 226 affixed to the end of lower half-pipe 242 so that when the lead screw 208 turns, the carriage 212 moves axially causing the upper half-pipe 242 to move axially with it.

The lead screw 208 has a lead screw gear 202 affixed to an end thereof for driving the lead screw 208. Similarly, the lead screw 206 has a lead screw gear 204 affixed to an end thereof for driving the lead screw 206. The cutter extension 220 is driven axially by a cutter screw 214 which is rotated by a cutter gear 215. The cutter screw 214 is threaded in a nut which is affixed to a disposable chassis 218.

The lead screw gear 202 engages a pinion 252 in the durable component 251. The lead screw gear 204 engages a pinion 254 in the durable component 251. The cutter gear 215 engages a pinion 256 in the durable component 251. Motor/transmission drives 264, 256 and 260 are connected to rotate pinions 252, 254, and 256, respectively. The lead screw gears 202 and 204 and the cutter gear 215 engage the pinions 252, 254, and 256 when the disposable component 201 is attached to the durable component 251 with the durable component and the disposable chassis 218 registering the various components.

Referring now also to FIGS. 4A to 4D, it should be clear from the above description that when the lead screw gears 202 and 204 and the cutter gear 215 engage the pinions 252, 254, and 256, respectively, the cutting cannula 20, the sheath 12, and the stylet 10, can be moved independently by controlling the motor/transmission drives 260, 256 and 264, respectively. Therefore, the above embodiment permits a sample to be taken into the sample port 210A, in accord with the embodiment of FIGS. 4A to 4D and moved to a chamber port 244 in the cutter extension where it can be recovered.

A controller (not shown) may be configured to control the motor/transmission drives 260, 256 and 264 such that the following operation sequence can be realized to obtaining a sample and deliver it to the port 244. Note that the port 244 corresponds, in this embodiment, to the sample recovery port 20A or sample acquisition recess 10A of the embodiments of FIGS. 3A to 4D as described above. The procedure may be as follows.

1. Upon insertion of the disposable component 201, assert home position in which the cutting cannula 20 and the stylet 10 are fully extended toward the needle distal end and sheath 12 is retracted to the position shown in FIG. 4A. This is done by running motor transmission drives 260, 256 and 264 to registration positions, where respective (limit) switches are triggered, and counting the pulses of respective encoders. The indication of insertion may be by means of a switch (not shown) on the durable component 251 triggered by a boss (not shown) on the chassis 218. The registration may be followed by the retraction of the chassis 218 in preparation for a thrusting operation as is known for biopsy needles.

2. Upon receipt of a command (e.g., a control panel switch) to obtain a sample, a vacuum pump (not shown, but preferably a component such as a syringe is provided in the disposable component 201 and a mating drive is provided in the durable component 251) is operated to obtain an initial vacuum.

3. As soon an initial vacuum is generated, the cutting cannula 20 is retracted by running motor/transmission drive 260 while counting pulses of an encoder to a proximal stop point. Alternatively control signaling can be provided by a limit switch.

4. After a programmed interval, following the retraction of the cutting cannula 20, the cutting cannula 20 is driven distally by operating the motor/transmission drive 260 while counting pulses of an encoder to a proximal stop point. Alternatively control signaling can be provided by a limit switch.

5. At the same time as the cutting operation, the sheath 12 may be driven distally so that it covers and protects the sample from frictional engagement with the surrounding surfaces (e.g., the cannula 20) when the stylet 10 and sheath 12 are moved proximally. The sheath 12 may be driven distally at a later time. The sheath 12 may be driven by operating the motor/transmission drive 256 while counting pulses of an encoder to a distal stop point or according to signals of a limit switch.

6. At this point, the sample is covered by the sheath 12 and stylet 10 may be retracted to the port 244. This may be done by operating the motor/transmission drives 256 and 264 simultaneously while counting pulses of an encoder to a distal stop point or according to signals of a limit switch. Preferably the rotation of the drives is synchronized to keep the sheath 12 and stylet 10 together as they travel to the port 244.

7. After the sample reaches the port 244, the sheath 12 may be further retracted to uncover the sample for extraction through the port 244. The sample may be ejected as described above, for example using a puff of air or saline or both.

In the present embodiment, the upper and lower half-pipes 242 and 224 are equal-diameter hemi-cylindrical elements that slide within cutter extension 220, which defines a full cylinder. However, other arrangements are possible, such as one in which all three, upper and lower half-pipes 242 and 224 and the cutter extension 220 define full cylinders which are arranged coaxially, or where upper and lower half-pipes 242 and 224 are replaced by rods which are connected to the sheath 12 and stylet 10 toward the distal end of the stylet 10.

Figure 12A:
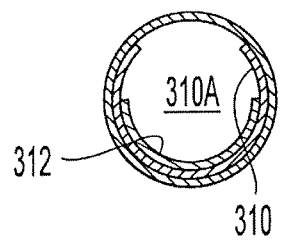
FIGS. 12A and 12B illustrate an alternative embodiment of a cutting cannula, stylet and sheath.
Figure 12B:
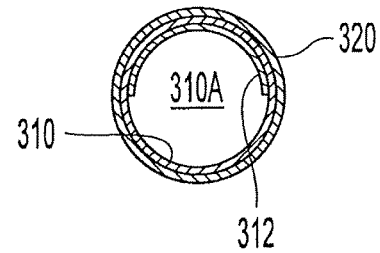

FIGS. 12A and 12B illustrate an alternative embodiment of a cutting cannula 320, stylet 310 and sheath 312 which may be implemented with a coaxial arrangement of the cutting cannula 320, stylet 310 and sheath 312 whose functions are similar to cutting cannula 20, stylet 10 and sheath 12 but where instead of the sheath 12 being positioned over the sample by displacing it in an axial direction, the sheath 312 is rotated about a common axis of the assembly. In FIG. 12A, the arrangement is shown with the sheath 312 in position for receiving or ejecting a sample or for cutting. In FIG. 12B, the arrangement is shown with the sheath 312 in position for transporting the sample through the cutting cannula 320.

Referring to FIG. 13, in all of the above embodiments, various motors, drives, valves, and other actuators are variously described along with their respective operations and operational sequences. It is clear from the particulars of each embodiment that a device may employ a controller 350 such as a programmable microprocessor controller, to provide the described functionality.

While the present invention has been disclosed with reference to certain preferred embodiments, numerous modifications, alterations, and changes to the described embodiments are possible without departing from the sphere and scope of the present invention, which is described, by way of example, in the appended numbered paragraphs below. Accordingly, it is intended that the present invention not be limited to the described embodiments, but that it have the full scope defined by the language of at least the following paragraphs, and equivalents thereof.

The invention claimed is:

1. A method of operating a biopsy device, comprising:
    positioning a stylet, movable within a cutting cannula, such that a sample acquisition recess of the stylet is positioned at a sample receiving position, relative to the cutting cannula, wherein the cutting cannula is disposed proximally to the sample acquisition recess of the stylet;
    operating the cutting cannula to cut a tissue sample from adjacent tissue, the tissue sample being received in the sample acquisition recess of the stylet;
    extending a cover member between the stylet and the cutting cannula such that the cover member extends over the tissue sample in the sample acquisition recess of the stylet to contain the tissue sample between the cover member and the stylet; and
    moving the stylet, the cover member, and the tissue sample in unison relative to the cutting cannula proximally from the sample receiving position to a sample recovery position, while the cutting cannula is stationary.

2. The method of claim 1, comprising repeating the acts of positioning, operating, extending, and moving to collect another tissue sample.

3. The method of claim 1, wherein following the act of moving the stylet, the cover member, and the tissue sample in unison while the cutting cannula is stationary, the method further including moving the cover member relative to the stylet to expose the tissue sample at a recovery opening in the cutting cannula.

4. The method of claim 1, wherein the act of receiving the tissue sample in the sample acquisition recess of the stylet includes receiving the tissue sample adjacent a bulkhead affixed to the stylet, the bulkhead pushing the tissue sample as the stylet is moved.

5. The method of claim 1, wherein prior to operating the cutting cannula, further comprising suctioning into the sample acquisition recess in the stylet the tissue from which the tissue sample is collected.

6. The method of claim 1, wherein the extending includes axially moving the cover member relative to the stylet and the cutting cannula.

7. The method of claim 1, comprising deploying a tissue marker from a tip of the stylet.

8. The method of claim 1, comprising partially retracting the cover member at the sample recovery position to partially expose the tissue sample while forcing a quantity of pressurized fluid into a space below the cover member to eject the tissue sample from the sample acquisition recess of the stylet.

9. A biopsy device, comprising:
    a cannula having a proximal end, a distal end, a distal opening at the distal end, and a recovery opening at the proximal end;
    a first elongate element having a first distal end and a sample acquisition recess proximal to the first distal end;
    a second elongate element having a second distal end, each of the first elongate element and the second elongate element configured to move within the cannula between the distal opening of the cannula and the recovery opening of the cannula;
    the first elongate element and the second elongate element configured for movement with respect to each other, wherein in an open configuration the second distal end of the second elongate element is proximal to the sample acquisition recess of the first elongate element, and in a closed configuration the second elongate element extends over the sample acquisition recess of the first elongate element to surround a volume between the first elongate element and the second elongate element; and
    a drive unit coupled to each of the first elongate element and the second elongate element to configure the first elongate element and second elongate element in the open configuration and to configure the first elongate element and second elongate element in the closed configuration, the drive unit configured to move the first elongate element and the second elongate element in unison to move the volume of the closed configuration proximally to the recovery opening of the cannula.

10. The biopsy device of claim 9, wherein the drive unit is configured to move the first elongate element and second elongate element toward the distal opening of the cannula after the first elongate element and second elongate element are moved to the recovery opening of the cannula.

11. The biopsy device of claim 9, wherein the drive unit is configured to move the first elongate element and second elongate element into the open configuration after moving the volume of the closed configuration proximally to the recovery opening of the cannula.

12. The biopsy device of claim 9, the distal end of the cannula distal end has a cutting edge, and the drive unit configured to move the cutting edge of the cannula over the sample acquisition recess, and to thereafter configure the first elongate element and the second elongate element in the closed configuration.

13. The biopsy device of claim 9, wherein the first elongate element has a first bulkhead and a second bulkhead, and the sample acquisition recess is positioned between the first bulkhead and the second bulkhead.

14. The biopsy device of claim 9, wherein the first elongate element is a stylet and the second elongate element is a sheath, the sheath being interposed between the stylet and the cannula.

15. The biopsy device of claim 9, wherein the first elongate element and the second elongate element are shaped like half-cylinders arranged in mirror-image fashion.

* * * * *